US008228370B2

(12) United States Patent
Namii et al.

(10) Patent No.: US 8,228,370 B2
(45) Date of Patent: Jul. 24, 2012

(54) STEREOSCOPIC IMAGE SHOOTING AND DISPLAY SYSTEM

(75) Inventors: Yasushi Namii, Hachioji (JP); Junichi Nozawa, Sagamihara (JP)

(73) Assignee: Olympus Medical Systems Corp., Tokyo (JP)

(*) Notice: Subject to any disclaimer, the term of this patent is extended or adjusted under 35 U.S.C. 154(b) by 561 days.

(21) Appl. No.: 12/549,856

(22) Filed: Aug. 28, 2009

(65) Prior Publication Data

US 2010/0053308 A1 Mar. 4, 2010

(30) Foreign Application Priority Data

Sep. 2, 2008 (JP) .................................. 2008-224917

(51) Int. Cl.
H04N 15/00 (2006.01)
(52) U.S. Cl. .............................. 348/46; 348/43; 348/51
(58) Field of Classification Search .................... 348/43, 348/46, 51
See application file for complete search history.

(56) References Cited

U.S. PATENT DOCUMENTS

| 5,483,336 | A | * | 1/1996 | Tocher | 356/3.15 |
| 2010/0053308 | A1 | * | 3/2010 | Namii et al. | 348/47 |
| 2011/0025825 | A1 | * | 2/2011 | McNamer et al. | 348/46 |
| 2012/0044330 | A1 | * | 2/2012 | Watanabe | 348/54 |
| 2012/0105609 | | * | 5/2012 | Qi | 348/54 |

FOREIGN PATENT DOCUMENTS

JP 06-261860 9/1994

* cited by examiner

*Primary Examiner* — Michael Won
(74) *Attorney, Agent, or Firm* — Scully, Scott, Murphy & Presser, P.C.

(57) ABSTRACT

A stereoscopic image shooting and display system has a left-right pair of image pickup sections having a left-right pair of optical systems with a parallax, and an image processing section which performs predetermined image processing on left and right images picked up through the left-right pair of image pickup sections and parallactically different from each other, and which outputs the processed images to a display section to display the images as a stereoscopic image. When a region corresponding to a region difficult for an observer to observe is detected, the image pickup sections or the image processing section is controlled so that the region becomes easy-to-observe state.

20 Claims, 17 Drawing Sheets

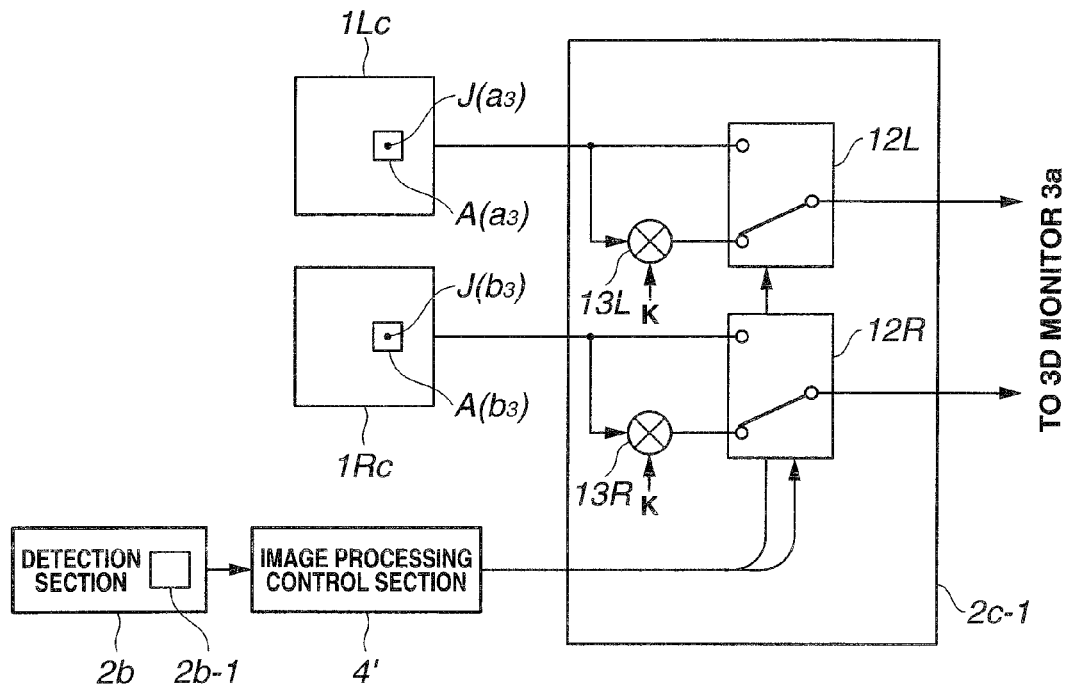
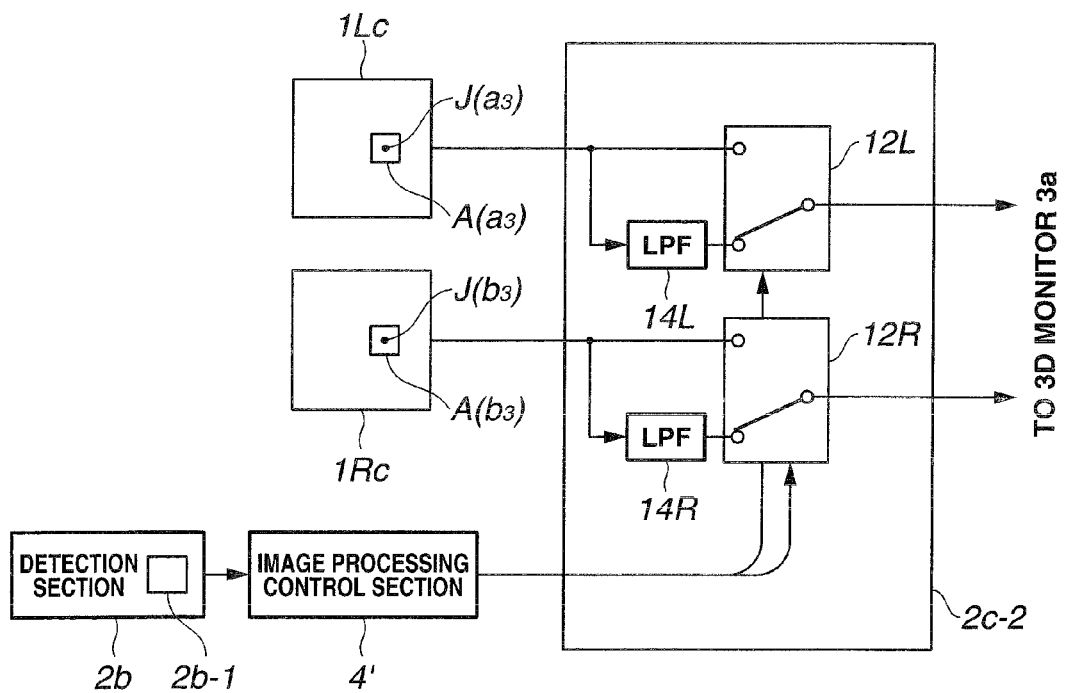

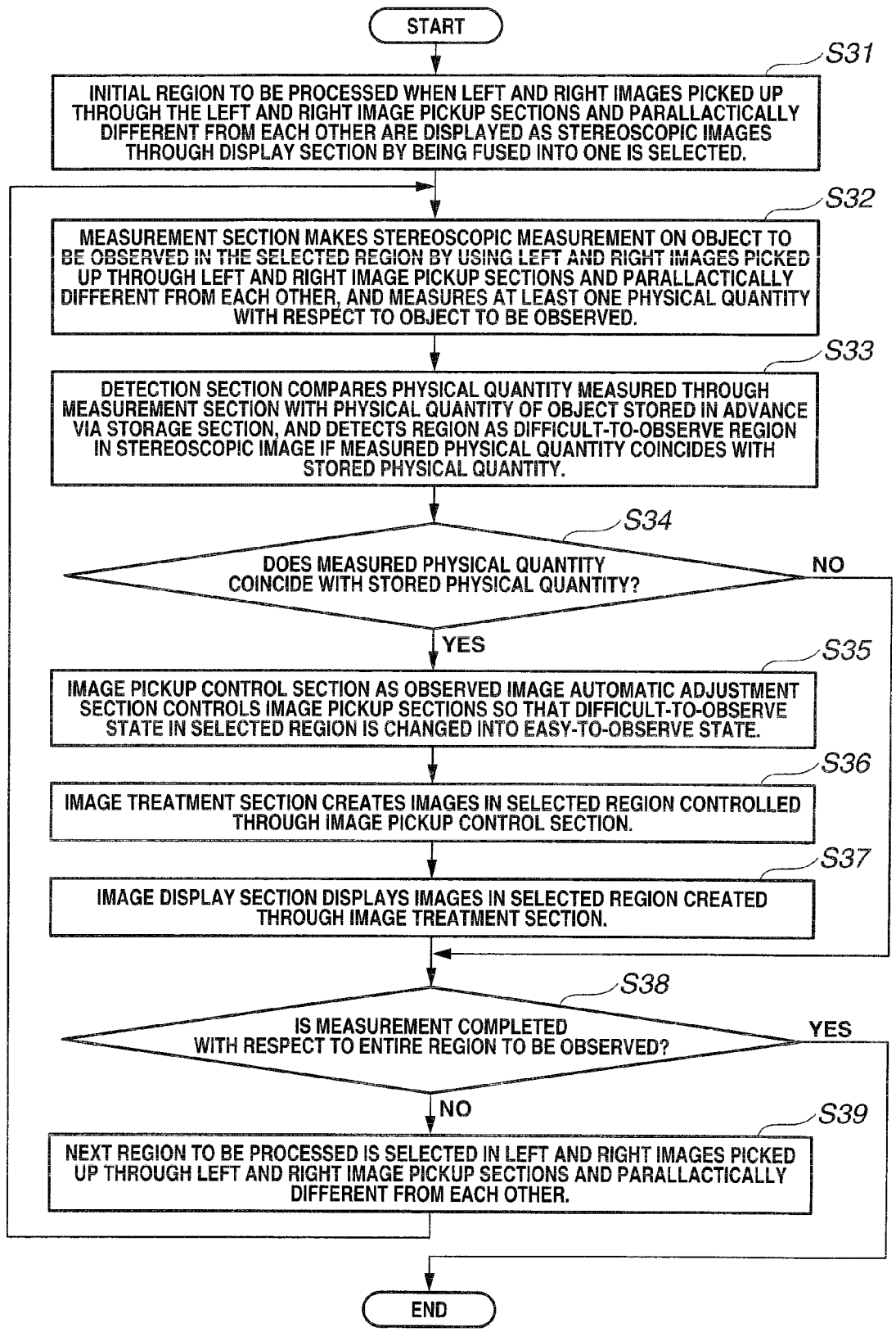

STEREOSCOPIC IMAGE SHOOTING AND DISPLAY SYSTEM

CROSS REFERENCE TO RELATED APPLICATION

This application claims benefit of Japanese Application No. 2008-224917 filed in Japan on Sep. 2, 2008, the contents of which are incorporated by this reference.

BACKGROUND OF THE INVENTION

1. Field of the Invention

The present invention relates to a stereoscopic image shooting and display system used, for example, for observation of a stereoscopic image of a portion of a subject on which a surgical operation is performed by using an endoscope.

2. Description of the Related Art

As a stereoscopic image shooting and display system of this kind, an endoscope video display apparatus described in Japanese Patent Application Laid-Open Publication No. 6-261860, for example, is known.

FIG. 18A shows the placement and configuration of an observation optical system at a distal end of an endoscope insertion portion in the endoscope video display apparatus described in Japanese Patent Application Laid-Open Publication No. 6-261860, which is an example of an art relating to the present invention. FIG. 18B is a diagram for explaining a parallax adjustment operation of the observation optical system.

This video display apparatus is designed so that the visibility of a stereoscopic image of an object to be observed is improved by measuring the distances between image pickup devices and the object and enabling changing the stereoscopic angle (the amount of left-right parallax) according to the distances.

That is, as shown in FIG. 18A, the distances between a subject M and left and right solid-state image pickup devices 61 and 62 are measured by applying infrared rays from an infrared ray emitting section 52 in a distance measurement section 51 to the subject M and receiving the infrared rays reflected from the subject M with an infrared sensor 53. A control section (not shown in the figure) adjusts the parallax between the left and right solid-state image pickup devices 61 and 62 by driving a parallax adjustment mechanism (not shown in the figure) on the basis of the distances measured by the distance measurement section 51 so that a good stereoscopic image of the object to be observed is obtained.

In the video display apparatus in the related art, the space between the optical axes of the left and right solid-state image pickup devices 61 and 62 is moved to change the stereoscopic angle, as shown in FIG. 18B.

SUMMARY OF THE INVENTION

A stereoscopic image shooting and display system according to the present invention has a left-right pair of image pickup sections having a left-right pair of optical systems with a parallax, an image processing section which performs predetermined image processing on left and right images picked up through the left-right pair of image pickup sections and parallactically different from each other, and a display section which displays the images processed through the image processing section, enabling observation of a stereoscopic image of an object to be observed through the left-right pair of image pickup sections, the image processing section and the display section.

The image processing section has a measurement section having at least a function to make a stereoscopic measurement on the object to be observed, a detection section which, when the left and right images parallactically different from each other are displayed as a stereoscopic image through the display section, detects the existence/nonexistence of a difficult-to-observe region in the stereoscopic image on the basis of results obtained through the measurement section, and an image treatment section which performs a predetermined image treatment on the left and right images picked up through the image pickup sections and parallactically different from each other.

The stereoscopic image shooting and display system further has a control section which, when the difficult-to-observe region is detected through the detection section, controls the image pickup sections or the image processing section so that image display on the display section is performed by changing the detected difficult-to-observe state in the difficult-to-observe region into an easy-to-observe state, in a state where the distance between the optical axes of the left-right pair of optical systems with a parallax is fixed.

BRIEF DESCRIPTION OF THE DRAWINGS

FIG. 4B is a diagram showing an example of a configuration in a case where the image treatment section performs partially darkening processing;

FIG. 4C is a diagram showing an example of a configuration in a case where the image treatment section changes a frequency characteristic;

FIG. 17 is a flowchart showing a processing procedure for displaying images of an object to be observed shot with the stereoscopic image shooting and display system in the third embodiment;

DETAILED DESCRIPTION OF THE PREFERRED EMBODIMENTS

Figure 1:
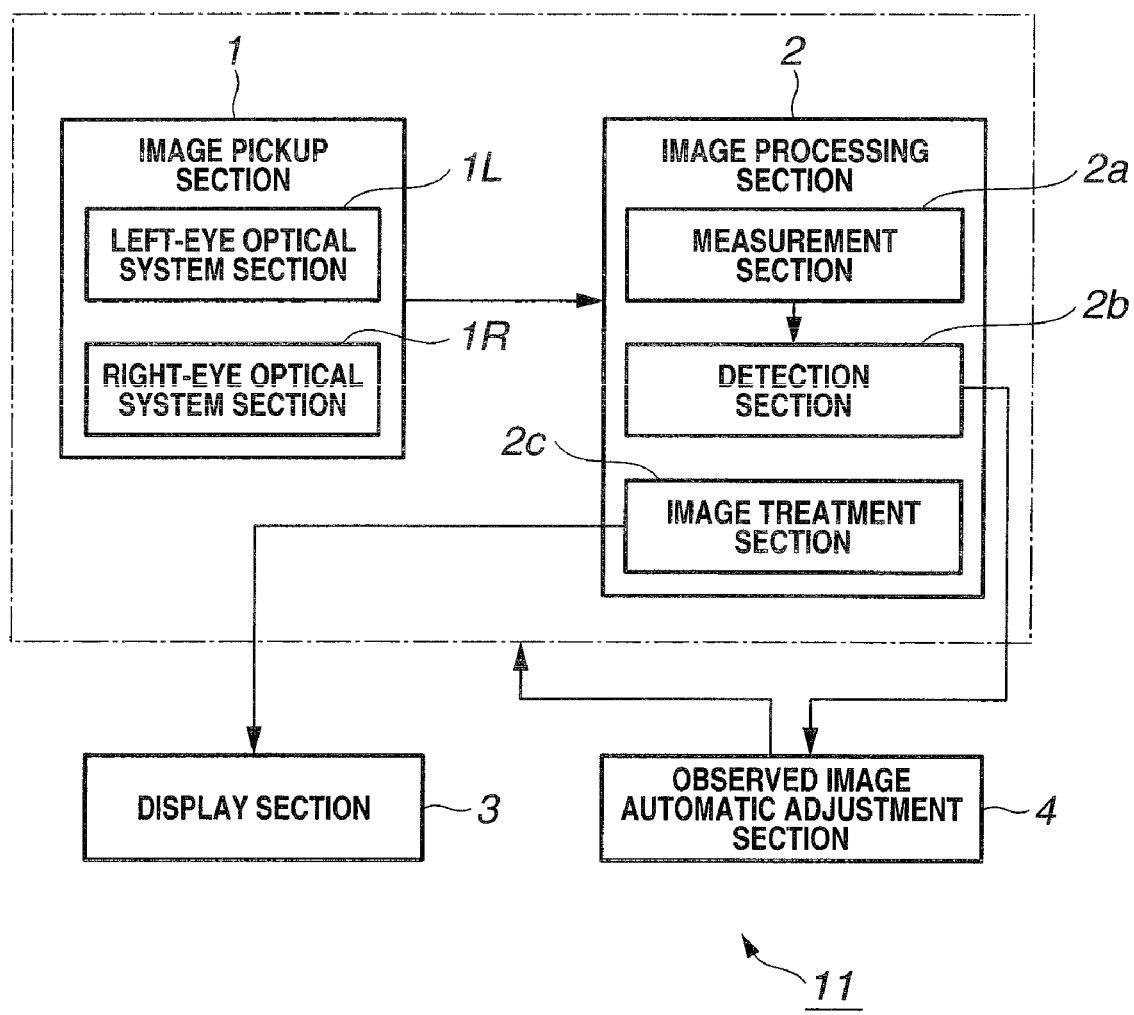
FIG. 1 is a block diagram schematically showing an example of a basic configuration of a stereoscopic image shooting and display system according to the present invention.

The present invention will be described based on embodiments shown in the drawings.

Figure 18A:
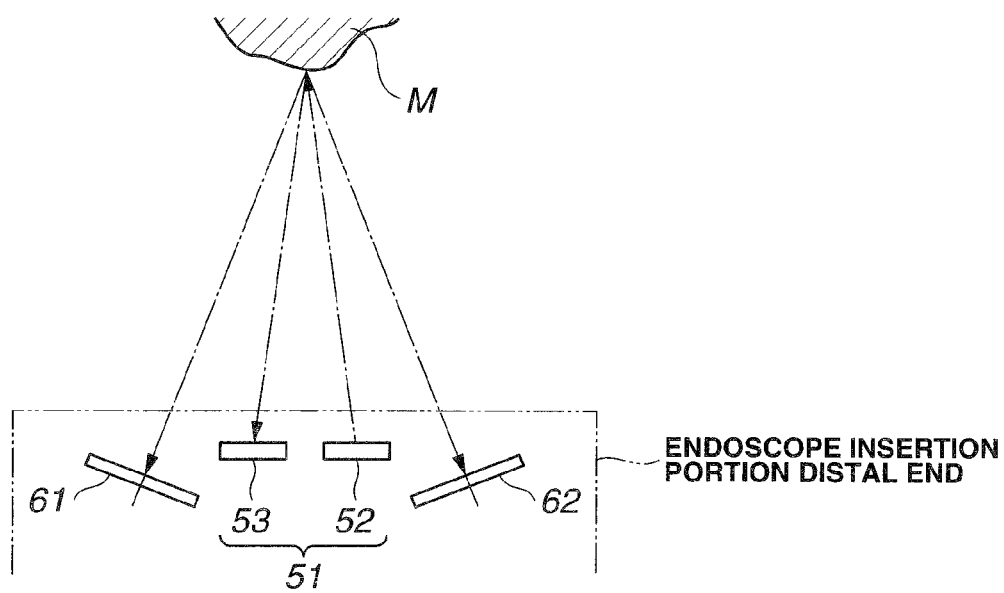
FIG. 18A is a diagram showing the placement and configuration of an observation optical system at a distal end of an endoscope insertion portion in an endoscope video display apparatus described in the related art.
Figure 18B:
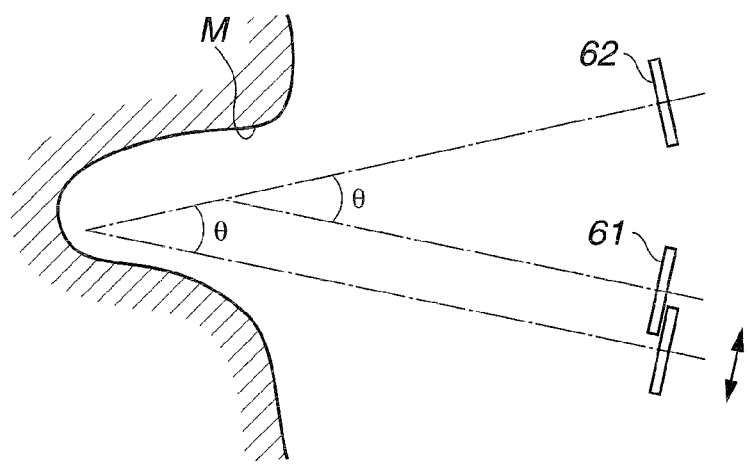
FIG. 18B is a diagram for explaining a parallax adjustment operation in the related art shown in FIG. 18A.

In the above-described related art, the size of the image pickup unit is increased in the diametral direction because of the configuration designed to move the space between the optical axes of the left and right solid-state image pickup devices 61 and 62 in order to change the stereoscopic angle as shown in FIG. 18B.

The facility with which an instrument such as an endoscope in particular is inserted into a patient is reduced if the diameter of the image pickup unit is increased. As a result, the physical burden on the patient is increased.

In ordinary cases, a body portion on which an operation is to be performed is not flat; it includes recesses/projections. Therefore, a portion of an image displayed on a monitor when a body portion having recesses/projections is stereoscopically observed sometimes appears to be largely projecting or recessed differently from a state actually observed with naked eyes.

In a case where an image stereoscopically observed has a portion which appears to be largely projecting or recessed differently from a state actually observed by a naked-eye observer, the observer has a feeling of unnaturalness in the stereoscopic observed image. Stereoscopic observation tends to become difficult to achieve in such a case. In the first embodiment, such a problem is solved.

A stereoscopic image shooting and display system in the first embodiment has a left-right pair of image pickup sections having a left-right pair of optical systems with a parallax, and an image processing section which performs predetermined image processing on left and right images picked up through the left-right pair of image pickup sections and parallactically different from each other, and which outputs the processed images to a display section which displays the images.

The image processing section has a measurement section having at least a function to make a stereoscopic measurement on the object to be observed by using the left and right images picked up through the left-right pair of image pickup sections and parallactically different from each other, a detection section which, when the left and right images parallactically different from each other are displayed as a stereoscopic image through the display section, detects the existence/nonexistence of a difficult-to-observe region in the stereoscopic image on the basis of results obtained through the measurement section, and an image treatment section which performs a predetermined image treatment on the left and right images picked up through the image pickup sections and parallactically different from each other.

The stereoscopic image shooting and display system further has a control section which, when the difficult-to-observe region is detected through the detection section, controls the image pickup sections or the image processing section so that image display on the display section is performed by changing the difficult-to-observe state in the detected difficult-to-observe region into an easy-to-observe state, in a state where the distance between the optical axes of the left-right pair of optical systems with a parallax is fixed.

Further, the present invention has the following main features, as described with respect to embodiments thereof.

In the stereoscopic image shooting and display system according to the present invention, the measurement section has a function to compute an image fusion position at which the left and right images parallactically different from each other are fused into one image, and the detection section computes, with respect to each region in the stereoscopic image when the left and right images parallactically different from each other are displayed as the stereoscopic image through the display section, the ratio of the second distance from a display surface of the display section to the image fusion position at which the left and right images parallactically different from each other computed through the measurement section are fused into one and the first distance from an observer to the display surface of the display section, and detects the region as a difficult-to-observe region in the stereoscopic image if the computed ratio satisfies the following condition expression (1):

$$25\% < H/M \tag{1}$$

Where M is the first distance from the observer to the display surface of the display section, and H is the amount of projection of the image fusion position from the display surface corresponding to the second distance from the display surface of the display section to the image fusion position of the left and right images parallactically different from each other computed through the measurement section.

In the stereoscopic image shooting and display system according the present invention, the detection section detects the region as a difficult-to-observe region in the stereoscopic image if the following condition expression (2) is satisfied in place of the condition expression (1) shown above.

$$15\% < H/M \quad (2)$$

In the stereoscopic image shooting and display system according to the present invention, the control section includes an image processing control section which makes the image treatment section convert a predetermined image characteristic in the difficult-to-observe region in the stereoscopic image so as to achieve an easy-to-observe state.

In the stereoscopic image shooting and display system according to the present invention, the image processing control section makes the image treatment section convert the difficult-to-observe region in the stereoscopic image from a three-dimensional image into a two-dimensional image.

In the stereoscopic image shooting and display system according to the present invention, the image processing control section makes the image treatment section convert the entire region in the stereoscopic image from a three-dimensional image into a two-dimensional image.

In the stereoscopic image shooting and display system according to the present invention, the image processing control section makes the image treatment section change the brightness in the difficult-to-observe region in the stereoscopic image.

In the stereoscopic image shooting and display system according to the present invention, the image processing control section makes the image treatment section change a frequency characteristic in the difficult-to-observe region in the stereoscopic image.

In the stereoscopic image shooting and display system according to the present invention, the control section is formed of an image pickup control section which performs predetermined control on the left-right pair of image pickup sections so that a predetermined image characteristic in the difficult-to-observe region in the stereoscopic image becomes easy-to-observe state.

In the stereoscopic image shooting and display system according to the present invention, the image pickup control section controls stops of the optical systems provided in the left-right pair of image pickup sections.

In the stereoscopic image shooting and display system according to the present invention, the image pickup control section controls focus positions of the optical systems provided in the left-right pair of image pickup sections.

In the stereoscopic image shooting and display system according to the present invention, the image pickup sections have an optical member common to the left-right pair of optical systems, and the image pickup control section controls a focus position through the common optical member provided in the left-right pair of image pickup sections.

The stereoscopic image shooting and display system according to the present invention further has a storage section which stores in advance at least one physical quantity of an object which can be a cause of generation of a difficult-to-observe region in the stereoscopic image when the left and right images parallactically different from each other are displayed as the stereoscopic image through the display section; the measurement section has a function to measure at least one physical quantity of the object to be observed; and the detection section compares, with respect to each region in the stereoscopic image when the left and right images parallactically different from each other are displayed as the stereoscopic image through the display section, the physical quantity of the object to be observed measured through the measurement section with the physical quantity of the object stored in the storage section in advance, and detects the region as a difficult-to-observe region in the stereoscopic image if the physical quantities coincide with each other.

In the stereoscopic image shooting and display system according to the present invention, the physical quantity is one of a shape size, a color, a three-dimensional shape and a spectral characteristic.

In the stereoscopic image shooting and display system according to the present invention, objects whose physical quantities are to be stored by the storage section include a treatment instrument.

Figure 2:
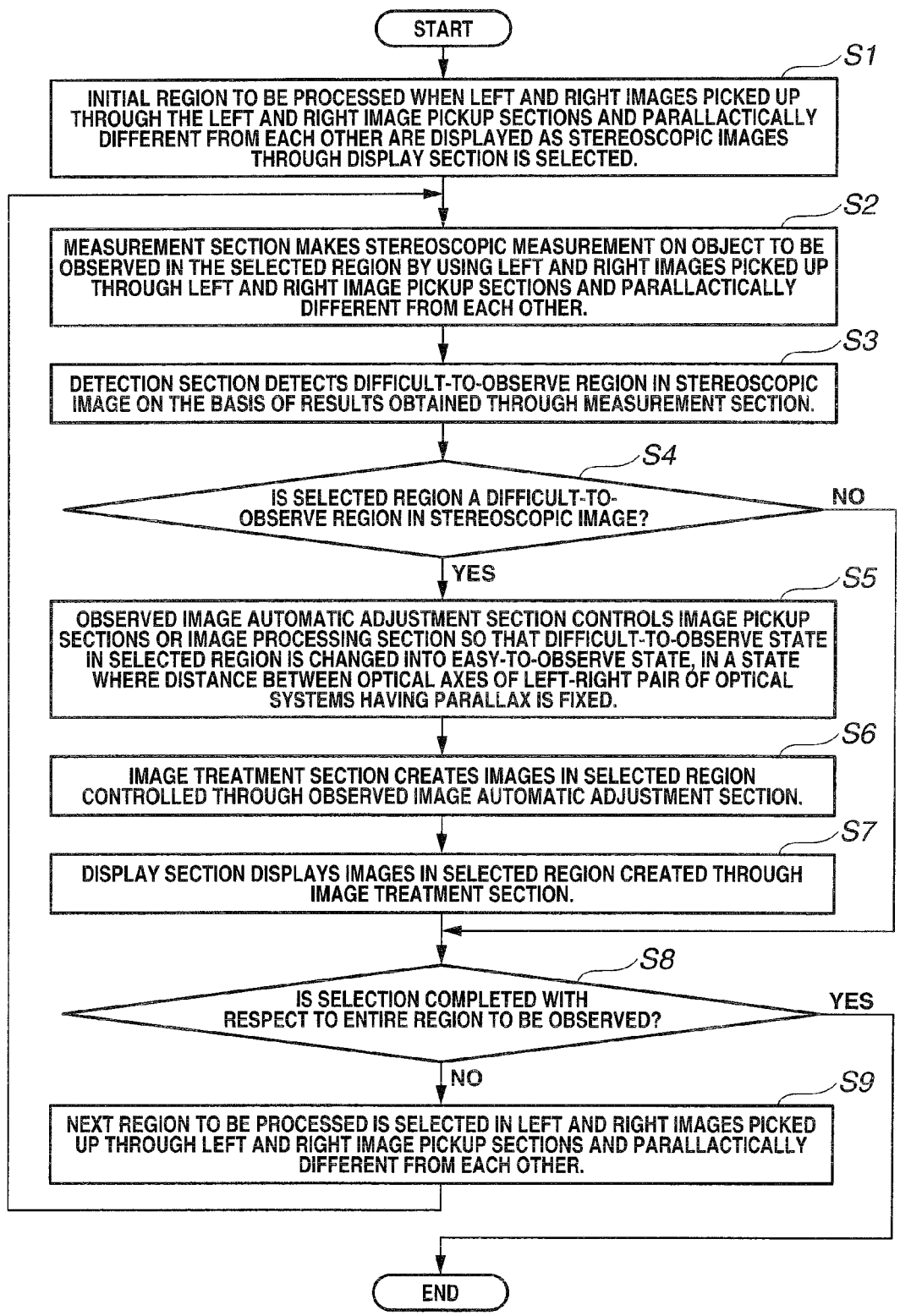
FIG. 2 is a flowchart showing a processing procedure for displaying images of an object to be observed shot with the stereoscopic image shooting and display system shown in FIG. 1.

FIG. 1 is a block diagram schematically showing an example of a basic configuration of a stereoscopic image shooting and display system 11 according to the present invention having the above-described features. FIG. 2 is a flowchart showing a processing procedure for displaying images of an object to be observed shot with the stereoscopic image shooting and display system shown in FIG. 1.

The stereoscopic image shooting and display system 11 shown in FIG. 1 has a left-right pair of image pickup sections 1, an image processing section 2 and a display section 3.

The left-right pair of image pickup sections 1 have a left-eye optical system section 1L and a right-eye optical system section 1 R as a left-right pair of optical systems with a parallax and are configured to pickup images in real time from an object to be observed.

The image processing section 2 performs predetermined image processing on left and right images picked up through the left-right pair of image pickup sections 1 and parallactically different from each other (or differing depending on a parallax) and outputs the processed images to the display section 3.

The display section 3 is configured to display as a stereoscopic image left and right images processed by the image processing section 2.

An observer observes through the display section 3 left and right images of an object to be observed (not shown in FIG. 1) picked up by the image pickup sections 1, and thereby perceives the left and right images as a stereoscopic image by fusing the left and right images into one. The form of display enabling perception of a stereoscopic image is described below.

In the stereoscopic image shooting and display system 11 shown in FIG. 1, the image processing section 2 includes a measurement section 2a, a detection section 2b and an image treatment section 2c. The stereoscopic image shooting and display system 11 further has an observed image automatic adjustment section 4 as a control section for performing such control as to facilitate observation with respect to the image processing section 2.

The measurement section 2a has at least a function to make a stereoscopic measurement on an object to be observed by using left and right images picked up through the left-right pair of image pickup sections 1 and parallactically different from each other.

The detection section 2b is configured to detect, when left and right images parallactically different from each other are displayed as a stereoscopic image through the display section 3, the existence/nonexistence of a region difficult for an observer to observe (hereinafter referred to as "difficult-to-observe region") in the stereoscopic image on the basis of results obtained through the measurement section 2a.

The image treatment section 2c is configured to perform a predetermined image treatment on left and right images picked up through the left-right pair of image pickup sections 1 and parallactically different from each other.

The observed image automatic adjustment section 4 is configured to control the image pickup sections 1 or the image processing section 2 when a difficult-to-observe region is detected through the detection section 2b, as described below. In a state where the distance between the optical axes of the left-right pair of optical system sections 1L and 1R with a parallax is fixed, the observed image automatic adjustment section 4 controls the image pickup sections 1 or the image processing section 2 so that the display section 3 produces an image display such that the difficult-to-observe state of the detected region is changed into an easy-to-observe state.

In the stereoscopic image shooting and display system 11 thus configured, the display section 3 displays images obtained by performing processing based on a processing procedure such as shown in FIG. 2 on images of an object to be observed picked up through the image pickup sections 1.

First, an initial region to be processed of left and right images picked up through the left-right pair of image pickup sections 1 and parallactically different from each other is selected when the left and right images are displayed as a stereoscopic image through the display section 3 (step S1).

Next, the measurement section 2a makes a stereoscopic measurement on the object to be observed in the selected region by using the left and right images picked up through the left-right pair of image pickup sections 1 and parallactically different from each other (step S2).

Next, the detection section 2b detects a difficult-to-observe region in the stereoscopic image on the basis of results obtained through the measurement section 2a (steps S3, S4).

If the selected region is detected as a difficult-to-observe region in the stereoscopic image, the observed image automatic adjustment section 4 controls the image pickup sections 1 or the image processing section 2 so that the difficult-to-observe state in the selected region is changed into an easy to observe state, in a state where the distance between the optical axes of the left-right pair of optical systems with a parallax is fixed (step S5). The image treatment section 2c then creates images controlled so as to be easy-to-observe state (step S6).

Next, the display section 3 displays the images in the selected region controlled through the observed image automatic adjustment section 4 and created through the image treatment section 2c (step S7).

Next, a check is made as to whether or not selection has been completed with respect to the entire region (step S8). If selection has not been completed, the next region to be processed is selected in the left and right images picked up through the left-right pair of image pickup sections 1 and parallactically different from each other (step S9), and processing from step S2 to step S8 is repeated.

In this way, the image observed by the observer is made easy to see as a whole.

Thus, in the stereoscopic image shooting and display system 11 according to the present invention, the image processing section 2 detects the existence/nonexistence of a difficult-to-observe region by using images picked up through the image pickup sections 1 and, if a difficult-to-observe region exists, the observed image automatic adjustment section 4 as a control section controls the image pickup sections 1 or the image processing section 2 so that the difficult-to-observe state in the selected region is changed into an easy-to-observe state, in a state where the distance between the optical axes of the left-right pair of optical systems with a parallax is fixed. Thus, a feeling of unnaturalness which an observer has in a stereoscopically observed image can be dissolved without thickening the image pickup sections 1 in the diametral direction.

First Embodiment

The first embodiment of the present invention will be described with reference to FIGS. 3 to 10.

Figure 3:
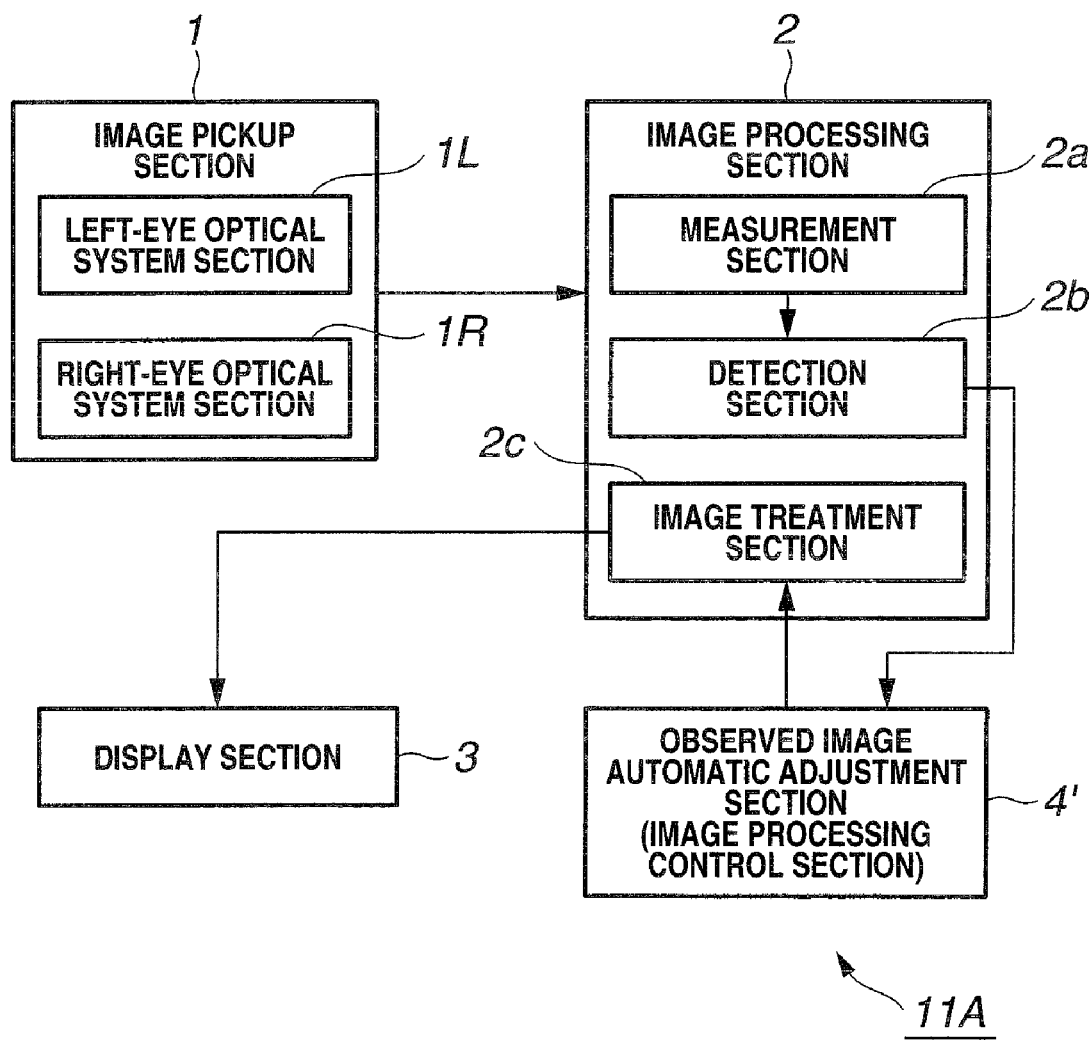
FIG. 3 is a block diagram schematically showing a configuration of a stereoscopic image shooting and display system according to a first embodiment of the present invention.

As shown in FIG. 3, a stereoscopic image shooting and display system 11A in the first embodiment has a left-right pair of image pickup sections 1, an image processing section 2 and a display section 3 and an observed image automatic adjustment section 4' as a control section.

The left-right pair of image pickup sections 1 have a left-eye optical system section 1L and a right-eye optical system section 1 R as a left-right pair of optical systems with a parallax and are configured to pickup images in real time from an object to be observed.

Figure 4A:
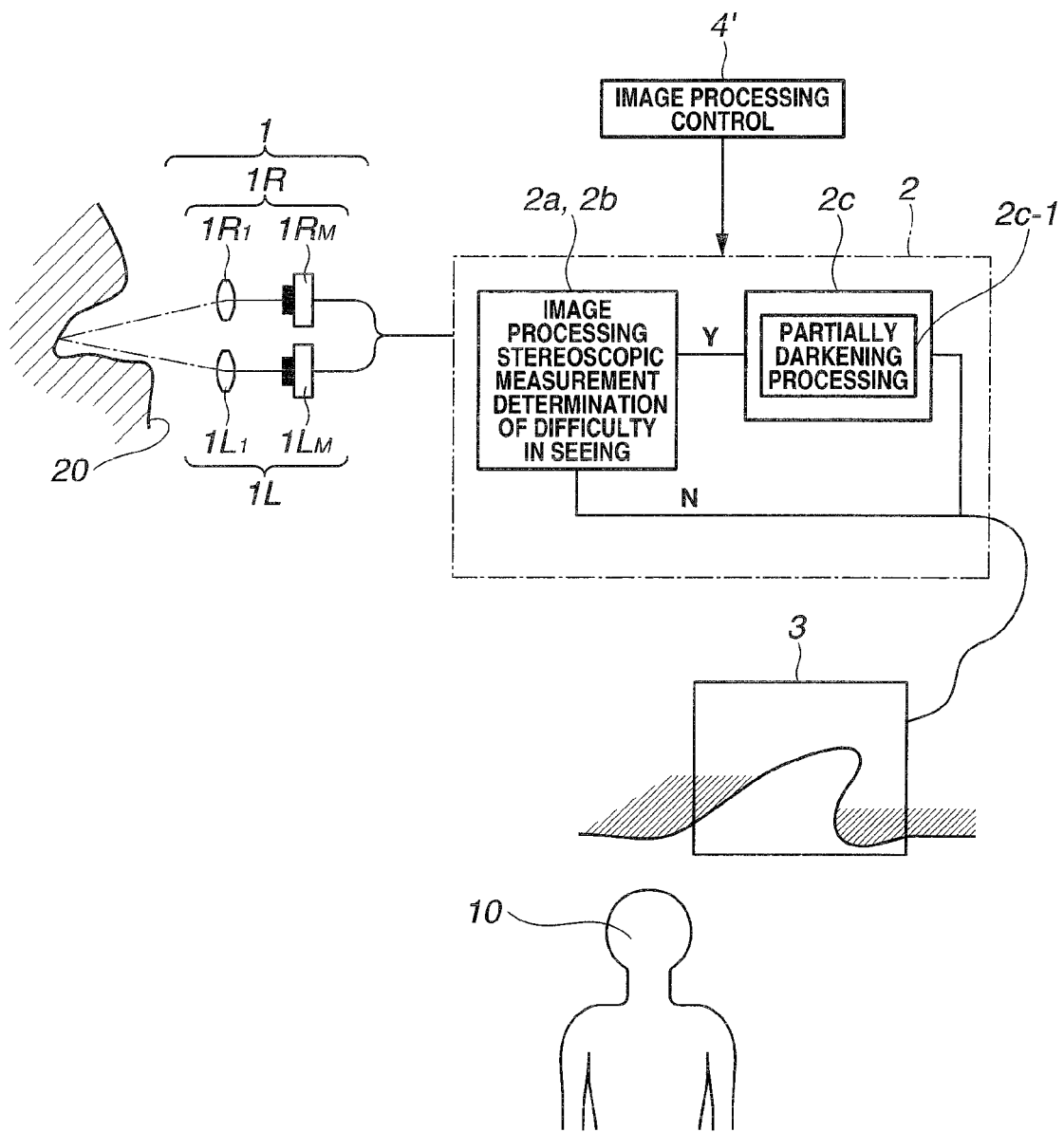
FIG. 4A is an explanatory diagram schematically showing an example of the entire configuration of the stereoscopic image shooting and display system shown in FIG. 3.

As shown in FIG. 4A, the left-eye optical system section 1L has a left-eye objective lens $1L_1$ and a left-eye image pickup device $1L_M$. The right-eye optical system section 1R has a right-eye objective lens $1R_1$ and a right-eye image pickup device $1R_M$.

Figure 5:
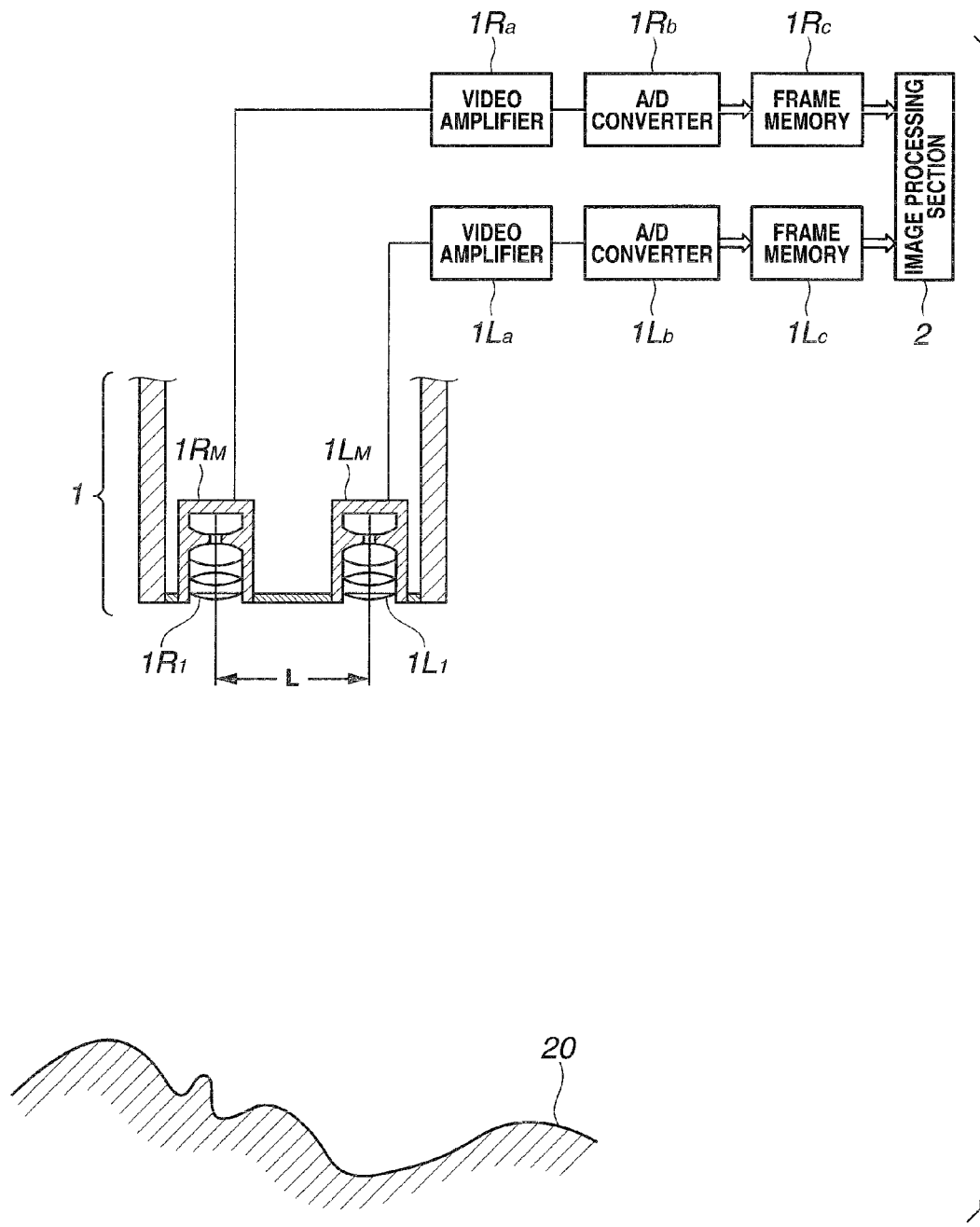
FIG. 5 is an explanatory diagram showing a concrete configuration from the image pickup sections to the image processing section in the stereoscopic image shooting and display system.

The left-right pair of objective lenses $1L_1$ and $1R_1$ are placed so as to have a predetermined distance L between their optical axes in the left-right direction (see FIG. 5). The left-right pair of objective lenses $1L_1$ and $1R_1$ are configured to form images of an object 20 to be observed on the left-right pair of image pickup devices $1L_M$ and $1R_M$, with the distance L set as a parallax. The left and right images of one object 20 to be observed formed on the left-right pair of image pickup devices $1L_M$ and $1R_M$ are formed as images different from each other due to the parallax L (also referred to as images parallactically different from each other).

The left-right pair of image pickup devices $1L_M$ and $1R_M$ are formed, for example, of charge-coupled devices (CCDs).

The left-right pair of image pickup sections 1 have, between the left-right pair of image pickup devices $1L_M$ and $1R_M$ and the image processing section 2, as shown in FIG. 5 for example, a left-right pair of video amplifiers $1L_a$ and $1R_a$, a left-right pair of A/D converters $1L_b$ and $1R_b$ and a left-right pair of frame memories $1L_c$ and $1R_c$. A configuration in which the image processing section 2 is provided with the video amplifiers $1L_a$ and $1R_a$ and so on may alternatively be adopted.

Output signals for left and right images picked up by the left and right image pickup devices $1L_M$ and $1R_M$ are respectively amplified by the video amplifiers $1L_a$ and $1R_a$ and converted into digital signals by the A/D converts $1L_b$ and $1R_b$. The digital signals for the left and right images are stored in the frame memories $1L_c$ and $1R_c$.

The left and right images (image data) stored in the frame memories $1L_c$ and $1R_c$ are images picked up with the parallax L, and the difference between the positions of points corresponding to each other in the two images of the object 20 to be observed includes three-dimensional information on the object 20 to be observed.

The groups of image data stored in the frame memories $1L_c$ and $1R_c$ are supplied to the image processing section 2. The image processing section 2 performs predetermined processing on the images on the basis of the groups of image data parallactically different from each other due to the distance L between the optical axes and computes recesses/projections of the object 20 to be observed and three-dimensional information such as lengths and areas.

The image processing section 2 includes, as shown in FIG. 3, a measurement section 2a, a detection section 2b and an image treatment section 2c.

The measurement section 2a has at least a function to make a stereoscopic measurement on the object 20 to be observed by using left and right images picked up through the left-right pair of image pickup sections 1 and parallactically different from each other.

The detection section 2b is configured to detect, when left and right images parallactically different from each other are displayed through the display section 3 as a stereoscopic image by being fused into one, the existence/nonexistence of a difficult-to-observe region in the stereoscopic image (or make determination as to difficulty in seeing the image) on the basis of results obtained through the measurement section 2a.

The image treatment section 2c is configured to perform a predetermined image treatment by using left and right images picked up through the left-right pair of image pickup sections 1 and parallactically different from each other.

The display section 3 is configured to display left and right images processed through the image processing section 2 as a stereoscopic image to enable an observer to perform stereoscopic observation.

As a mode of display of a stereoscopic image stereoscopically observable by an observer, a well-known mode of display can be used. For example, the display section 3 has a left and right display monitors which respectively display left and right images and to which polarizing plates are attached, and an observer observes the left and right images with his/her eyes by using polarized glasses.

Another mode of display is conceivable in which left and right images are displayed on a common 3D monitor by being alternately selected and stereoscopic observation is enabled by performing light transmission/blocking (ON/OFF) control of liquid crystal shutters in left and light glass portions in liquid crystal glasses put on by an observer in synchronization with the selection between the images. An example of a configuration for this mode of display is described in the publication of the above-described related art.

The observed image automatic adjustment section 4' functions as an image processing control section to make the image treatment section 2c convert a predetermined image characteristic in a difficult-to-observe region in a stereoscopic image to achieve an easy-to-observe state, when the difficult-to-observe region is detected through the detection section 2b.

The principle of three-dimensional information measurement in the measurement section 2a in the image processing section 2 will be described below.

Figure 6:
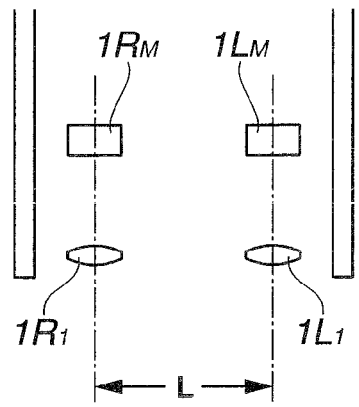
FIG. 6 is a diagram showing a left-right pair of image pickup optical systems constituting the image pickup sections in the stereoscopic image shooting and display system in the first embodiment.

As shown in FIG. 6, the image pickup devices $1R_M$ and $1L_M$ respectively pick up an image obtained through the right-eye objective lens $1R_1$ as a first viewpoint and an image obtained through the left-eye objective lens $1L_1$ as a second viewpoint, with the parallax L produced with respect to the predetermined distance L between the optical axes.

Figure 7:
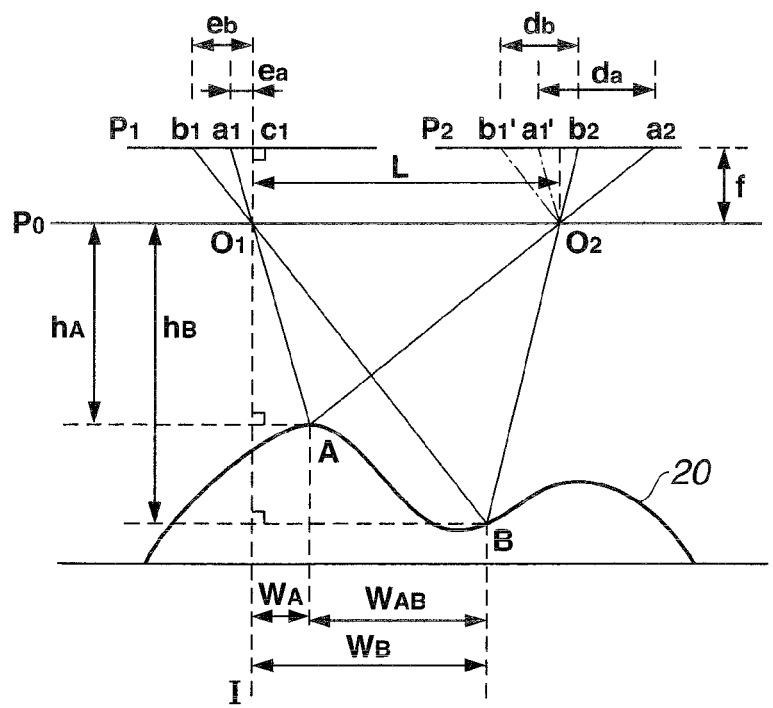
FIG. 7 is an explanatory diagram showing the principle of measure of three-dimensional information in the stereoscopic image shooting and display system in the first embodiment.

In this case, the geometrical correspondences between the images on the image pickup devices $1R_M$ and $1L_M$ and the object 20 to be observed are as shown in FIG. 7.

The positions of centers of the objective lenses $1R_1$ and $1L_1$ are indicated by $O_1$ and $O_2$; images obtained when the objective lenses are in these positions are indicated by $P_1$ and $P_2$; and the positions of the focal points of the objective lenses $1R_1$ and $1L_1$ are indicated by f.

In this case, arbitrary points A and B of the object 20 to be observed are respectively projected to positions $a_1$ and $b_1$ on the image $P_1$ and positions $a_2$ and $b_2$ on the image $P_2$. When these images are superposed one on another, the positions $a_1$ and $b_1$ correspond to positions $a_1'$ and $b_1'$ on the image $P_2$.

The distance between $a_1'$ and $a_2$ and the distance between $b_1'$ and $b_2$ when these images are superposed are represented by $d_a$ and $d_b$, respectively. Also, the distance between a plane $P_0$ containing the positions $O_1$ and $O_2$ and the point A of the object 20 to be observed is represented by $h_A$, and the distance between the plane $P_0$ and the point B is represented by $h_B$. Then the following relation equation (a) is established between the distances $h_A$ and $d_a$ because of the similarity relationship between a triangle $AO_1O_2$ and a triangle $O_2a_1'a_2$.

$$h_A/L=f/d_a \tag{a}$$

The distance $h_A$ can therefore be obtained by the following equation (b):

$$h_A=(f\cdot L)/d_a \tag{b}$$

Similarly, the distance $h_B$ can be obtained by the following equation (c):

$$h_B=(f\cdot L)/d_b \tag{c}$$

Thus, by obtaining the distances $d_a$ and $d_b$ between the corresponding points in the two images $P_1$ and $P_2$ parallactically different from each other due to the parallax L, absolute magnitudes $h_A$ and $h_B$ in a height direction at these points on the object 20 to be observed can be obtained.

This height direction corresponds to the direction of projection as a direction perpendicular to the display surface of the display section 3.

Description will next be made of a case where the absolute magnitude of the distance between arbitrary points on the object 20 to be observed is obtained.

The center in the image P1 is represented by $c_1$, and the distance between $c_1$ and $a_1$ and the distance between $c_1$ and $b_1$ on the image $P_1$ are represented by $e_a$ and $e_b$, respectively. Also, the distance between a straight line I extending from the position $O_1$ perpendicularly to the object 20 to be observed and the point A and the distance between the straight line I and the point B are represented by $W_A$ and $W_B$, respectively. Between the distance $W_A$ and the distance $e_a$, $$W_A/h_A=e_a/f \tag{d}$$

is established from the proportional relationship. $W_A$ can be obtained by substituting the above equation (b) in this equation (d), as shown by $$W_A=(e_a\cdot h_A)/f=(e_a\cdot f\cdot L)/(f\cdot d_a)=e_a\cdot L/d_a \tag{e}$$

Similarly, Wb can be obtained as shown by the following equation (f):

$$W_B=(e_b\cdot L)/d_b \tag{f}$$

Therefore the distance $W_{AB}$ between the point A and the point B when the object 20 to be observed is projected onto a plane parallel to the plane $P_0$ can be obtained as expressed by the following equation (g):

$$W_{AB}=W_B-W_A=L\{(e_b/d_b)-e_a/d_a)\} \tag{g}$$

In this way, the absolute magnitude of the distance between arbitrary points on the object 20 to be observed can be measured on the image $P_1$.

Description will next be made of a case where the distance d between corresponding points in the above-described two images $P_1$ and $P_2$ is obtained. This distance d can be obtained basically by examining a correlation in small regions in the two images $P_1$ and $P_2$.

Small regions in the two images $P_1$ and $P_2$ are expressed by functions f(r) and g(r) and it is assumed that the function g(r) is shifted by D relative to the function f(r). That is, g(r)=f(r−D) is assumed. In this equation, r is two-dimensional coordinates. The correlation between the function f(r) and the function g(r) is defined by the following equation (h):

$$\phi(S)=\int_A f(r)\cdot g^*(r-S)\cdot dr \tag{h}$$

Where A represents the area of the small areas. This equation (h) is shown in a simplified form: φ(s)=f(r)*g(r) hereinafter.

The above equation (h) is Fourier-transformed into $$\Phi(u)=F(u) \cdot G^*(u) \tag{i}$$

where F(u) represents a function into which the function f(r) is Fourier-transformed and G(u) represents a function into which the function g(r) is Fourier-transformed.

The condition g(r)=f(r−D) is used here to change the above equation (i) into $$\Phi(u)=F(u) \cdot F^*(u) \cdot e^{-j \cdot 2\pi \cdot u \cdot D} \tag{j}$$

This equation is inverse-Fourier-transformed into the following equation (k):

$$\phi(S)=R_{ff}(t)*\delta(t-D) \tag{k}$$

In this equation (k), $R_{ff}(t)$ is an autocorrelation function of f(r) and equation of $R_{ff}(t)$ by $$R_{ff}(t)=f(r)*f(r) \tag{l}$$

and the fact that the inverse Fourier transform of $e^{-j \cdot 2\pi \cdot u \cdot D}$ is a delta function δ(t−D) are used.

The above equation (k) indicates that the correlation function φ(S) has a peak at S=D. Therefore the amount of shift of the function g(r) relative to the function f(r) can be determined by obtaining the correlation function φ(S) and examining the position D of its peak.

By utilizing this, corresponding small regions are obtained from the two images $P_1$ and $P_2$ to obtain the distance d between corresponding points.

A determination index for detecting a difficult-to-observe region in the detection section 2b will be described with reference to FIGS. 8 and 9.

Figure 8:
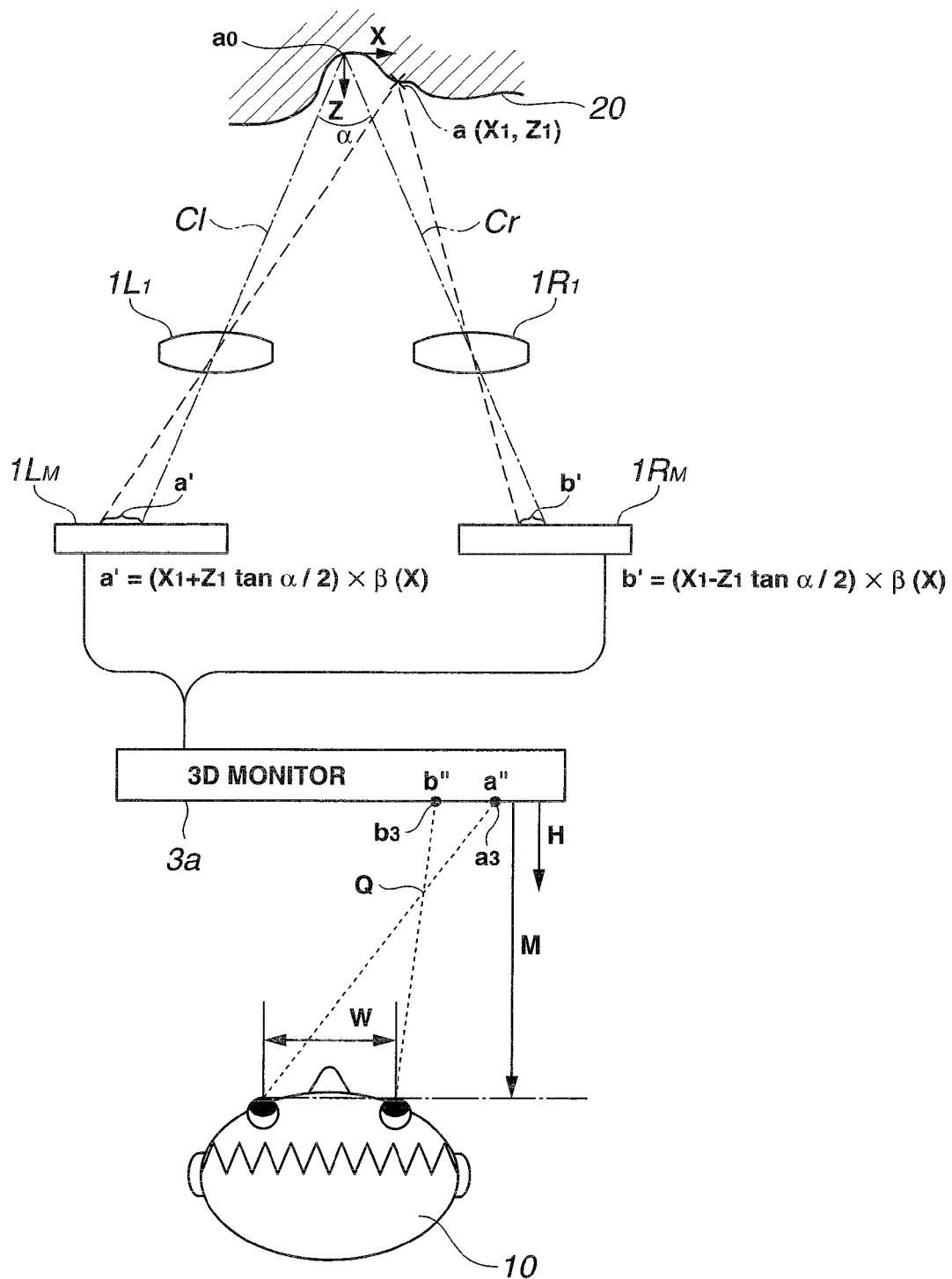
FIG. 8 is an explanatory diagram outlining a method of computing a position to which an image projects from a display surface when an object to be observed is stereoscopically observed in the stereoscopic image shooting and display system in the first embodiment.

FIG. 8 is a diagram outlining a method of computing a position to which an image projects when an observer stereoscopically observes the object 20 to be observed. FIG. 9 is an enlarged view showing the vicinity of the object to be observed in FIG. 8.

Description will be made of computation of an amount of projection H of a fusion image from the display surface of a 3D monitor 3a as the display section 3 in a case where an observer 10 observes through the 3D monitor 3a as the display section 3 an arbitrary point a($x_1$, $z_1$) of an object as the object 20 to be observed.

Figure 9:
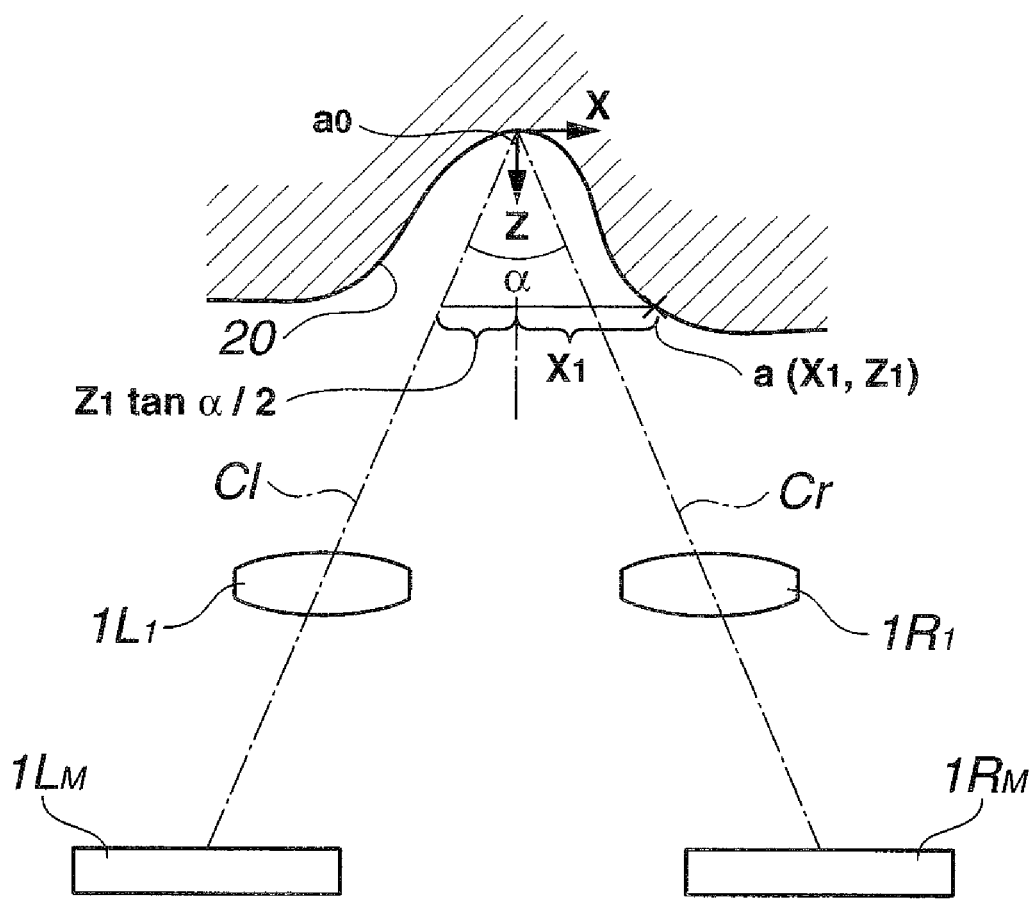
FIG. 9 is an explanatory diagram showing the vicinity of the object to be observed (subject) in FIG. 8.

First, the distance $a_x$ between the arbitrary point a($x_1$, $z_1$) stereoscopically measured through the measurement section 2a and the optical axis Cl of the left-eye optical system section 1L in the x-direction is $$x_1+\{z_1 \times \tan(\alpha/2)\}$$

from FIG. 9. Similarly, the distance $b_x$ between the arbitrary point a($x_1$, $z_1$) and the optical axis Cr of the right-eye optical system section 1R in the x-direction is $$x_1-\{z_1 \times \tan(\alpha/2)\}$$

Next, these distances $a_x$ and $b_x$ are considered as distances on the surfaces of CCDs $1L_M$ and $1R_M$. In this case, interposition of the objective lenses $1L_1$ and $1R_1$ entails multiplication of the distance in the x direction by a longitudinal magnifying factor β at the surfaces of the CCDs $1L_M$ and $1R_M$ as image pickup devices.

Therefore distances a' and b' from the optical axes Cl and Cr on the CCDs $1L_M$ and $1R_M$ corresponding to the distances $a_x$ and $b_x$ are $$a'=(x_1+z_1 \times \tan(\alpha/2)) \times \beta(x)$$

$$b'=(x_1-z_1 \times \tan(\alpha/2)) \times \beta(x),$$

as shown in FIG. 8. In these equations, β(x) is a longitudinal multiplying factor of the objective lenses $1L_1$ and $1R_1$ with respect to the distance in the x-direction.

When the observer 10 directly observes the object 20 to be observed with his/her eyes, he/she perceives as one image the left and right images formed on the left and right retinas and parallactically different from each other, by fusing the left and right images into one.

In that case, the observer 10 stereoscopically perceives the arbitrary point a($x_1$, $z_1$) in the object 20 to be observed according to the difference between the distances in the left and right images on the left and right retinas corresponding to the above-described distances a' and b'.

More specifically, the observer 10 stereoscopically perceives the point a ($x_1$, $z_1$) according to the difference between the distances corresponding to the above-described distances a' and b' as if the point projects toward the observer 10 by a projection amount z1 in the z-direction from a point $a_0$ in FIG. 8.

On the other hand, in the case of stereoscopic observation where the observer 10 observes the left and right images picked up by the image pickup sections 1 and displayed on the 3D monitor 3a to see the left and right images by fusing the left and right images into one as shown in FIGS. 8 and 9, stereoscopic observation can be performed in an easy-to-observe state if it is performed under a condition close to that in the case of naked-eye observation by the observer 10. On the other hand, stereoscopic observation under a condition largely different from that in the case of naked-eye observation is supposed to be difficult to perform.

Next, the amount of projection H from the display surface, serving as a major factor in an index for determination between an easy to stereoscopically observe state and a difficult to stereoscopically observe state in a case where the observer 10 observes the left and right images displayed on the display surface of the 3D monitor 3a, is computed.

When the above-described distances a' and b' are displayed on the 3D monitor 3a, if the display magnification of the size of the display surface of the 3D monitor 3a with respect to the size of the CCDs is r, the distances a" and b" on the 3D monitor 3a are $$a''=(x_1+z_1 \times \tan(\alpha/2)) \times \beta(x) \times r$$

$$b''=(x_1-z_1 \times \tan(\alpha/2)) \times \beta(x) \times r$$

The positions at two ends of the distances a" and b" on the 3D monitor 3a corresponding to the point a($x_1$, $z_1$) are indicated by $a_3$ and $b_3$, respectively, as shown in FIG. 8.

When the observer 10 observes the left and right positions $a_3$ and $b_3$ corresponding to the point a ($x_1$, $z_1$) on the left and right images on the 3D monitor 3a, he/she observes these points as a point at an image fusion position Q projecting by the projection amount H from the display surface of the 3D monitor 3a according to the difference between the distances a" and b".

Thus, the left and right points $a_3$ and $b_3$ are fused into one at the image fusion point Q at the second distance corresponding to the projection amount H from the display surface to be perceived as one image point by the observer 10.

The inventor of the present invention repeated an experiment to examine the difficulty in observation of stereoscopically observed images, by changing the ratio of the projection amount H and the first distance M from the observer 10 to the 3D monitor 3a as the display section 3.

It was thereby found that the index for determination of the difficulty in observation (seeing) of stereoscopically observed images was determined from the ratio of the projection amount H and the first distance M from the observer 10 to the 3D monitor 3a as the display section 3.

The ratio H/M of the projection amount H to the distance M is expressed here by the distances a″ and b″ on the 3D monitor 3a and the distance W between the eyes.

From FIG. 8, $$(M-H):H = W:(a''-b'')$$

is established. Therefore, $$H/M = (a'' - b'')/(W + a'' - b'')$$
$$= 2z_1 \times \tan(\alpha/2) \times \beta(x) \times r /$$
$$(W + 2z_1 \times \tan(\alpha/2) \times \beta(x) \times r)$$

It has been experimentally found that it is possible to determine that a stereoscopic image is difficult to see when the following condition expression (1) is satisfied.

$$25\% < H/M \quad (1)$$

In the stereoscopic image shooting and display system 11A in the first embodiment, the detection section 2b is configured to detect a difficult-to-observe region in a stereoscopic image when the computed ratio H/M satisfies the condition expression (1).

More preferably, a difficult-to-observe region in a stereoscopic image is detected when the following condition expression (2) is satisfied.

$$15\% < H/M \quad (2)$$

The image processing control section 4' controls the image treatment section 2c to perform processing for changing the brightness in a difficult-to-observe region in a stereoscopic image. For example, the image processing control section 4' controls the image treatment section 2c to perform partially darkening processing 2c-1 to facilitate observation by partially darkening a difficult-to-observe region, as shown in FIG. 4A.

FIG. 4B shows outline processing according to partially darkening processing 2c-1 in the image treatment section 2c. As shown in FIG. 4B, image data such as pixel values $J(a_3)$ and $J(b_3)$ at the positions $a_3$ and $b_3$ is stored in frame memories 1Lc and 1Rc.

These pixel values $J(a_3)$ and $J(b_3)$ are detected as corresponding image positions when the value of correlation between small regions $A(a_3)$ and $A(b_3)$ containing these pixel values peaks, and data on the positional relationship therebetween is stored, for example, in a memory 2b-1 in the detection section 2b.

The detection section 2b computes the ratio of the projection amount H to the distance M as described above with respect to these points $a_3$ and $b_3$ and determines whether or not the condition expression (1) or (2) is satisfied. The distance M and the projection amount H may be stored in the memory 2b-1.

The image processing control section 4' controls the image treatment operation of the image treatment section 2c by referring to the result of determination in the detection section 2b. For example, when the condition expression (1) is satisfied, the image treatment section 2c performs partially darkening processing 2c-1. A configuration in which the detection section 2b has the function of the image processing control section 4' may alternatively be adopted.

The image treatment section 2c has switches 12L and 12B for changing the pixel values (luminance values) in image data outputted from the frame memories 1Lc and 1Rc and outputting the pixel values, and multipliers 13L and 13R. A coefficient k smaller than 1 is input to each of the multipliers 13L and 13R.

When the image data satisfies the condition expression (1), the image processing control section 4' controls switching of the switches 12L and 12B so as to output the image data multiplied by the coefficient k with the multipliers 13L and 13R to the 3D monitor 3a, as indicated by the solid line in FIG. 4B.

In this case, a region appearing as a difficult-to-observe region after image fusion is displayed darkly. Therefore the function to identify a difficult-to-observe region by the observer 10 is reduced so as to change the difficult-to-observe state into an easy-to-observe state.

When the condition expression (1) is not satisfied, the image data is immediately outputted to the 3D monitor 3a by only being passed through the image treatment section 2c.

The condition expression (2) may be applied instead of the condition expression (1). A configuration in which the image processing control section 4' includes the image treatment section 2c or a configuration in which the image treatment section 2c includes the image processing control section 4' may alternatively be adopted.

Control of the image treatment section 2c by the image processing control section 4' may include making the image treatment section 2c perform filtering processing 2c-2 to change a frequency characteristic with respect to a difficult-to-observe region in a stereoscopic image.

FIG. 4C outlines a configuration in a case where the image treatment section 2c performs filtering processing 2c-2. The configuration shown in FIG. 4C includes filters 14L and 14R for transmission in a lower-frequency range (LPFs) with which the multipliers 13L and 13R in FIG. 4B are replaced.

The LPFs 14L and 14R have such a characteristic with respect to the signal band of image data as to allow low-frequency components of the image data to pass therethrough while suppressing (cutting) components on the higher-frequency sides. Control of switching of the switches 12L and 12B is performed, similarly to in the case shown in FIG. 4B.

With this configuration, when a difficult-to-observe region appears, high-frequency components of contour and structural portions in the region are suppressed to make the difficult-to-observe region easier to observe.

In this case, switching control may be performed on only one of the two LPFs 14L and 14R.

Control by the image processing control section 4' may also includes making the image treatment section 2c perform image treatment processing 2c-3 to convert a difficult-to-observe region into a two-dimensional image.

Figure 4D:
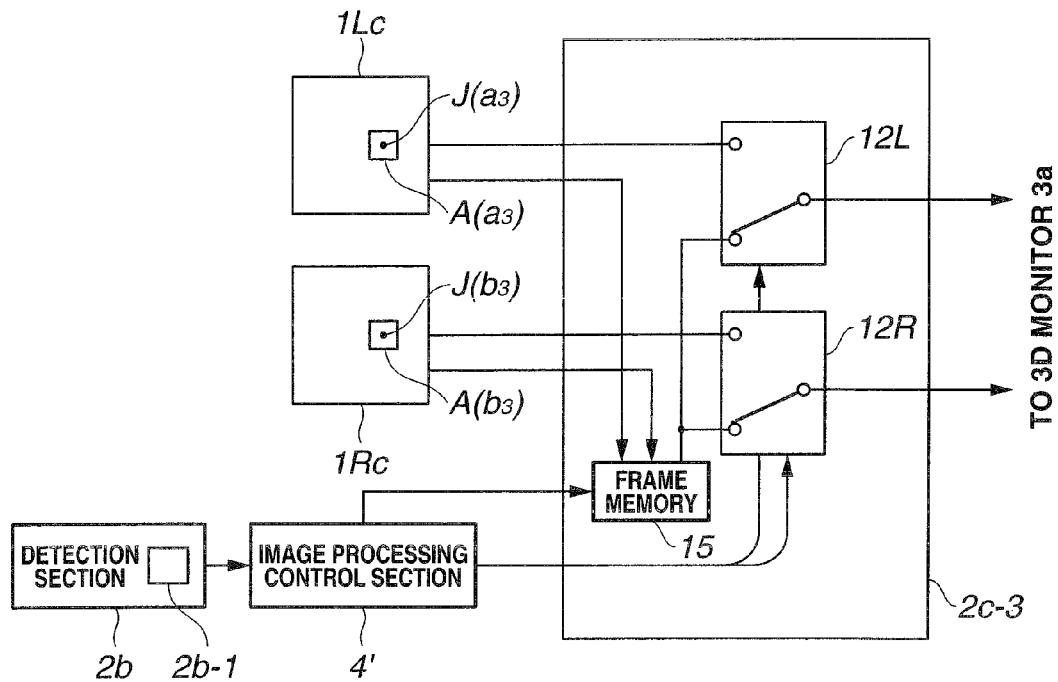
FIG. 4D is a diagram showing an example of a configuration in a case where the image treatment section performs processing for conversion into a two-dimensional image.

FIG. 4D shows an example of a configuration in a case where the above-described image treatment processing 2c-3 is performed in the image treatment section 2c. As for image treatment processing 2c-3 shown in FIG. 4D, the multipliers 13L and 13R are removed from the configuration shown in FIG. 4B, and image data is inputted from a frame memory 15 to the switches 12L and 12B.

For example, the image processing control section 4' generates common image data from left-image and right-image data outputted from frame memories 1Lc, 1Rc by using information from the memory 2b-1 in the detection section 2b, and stores the common image data in the frame memory 15.

In small area $A(a_3)$ and $A(b_3)$ portions containing corresponding pixel values $J(a_3)$ and $J(b_3)$ in two groups of image data, the two corresponding internal pixel values are averaged to form image data on the small areas $A(a_3)$ and $A(b_3)$.

When the condition expression (1) is satisfied as described above, the selector switches 12L and 12R are changed to output the common image data to the 3D monitor 3a. As a result, when the observer 10 observes a difficult-to-observe region portion, a common two-dimensional image corresponding to the portion is formed on the 3D monitor 3a and the difficult-to-observe portion is thereby made easier to observe.

Further, image treatment processing 2c-4 for converting the entire image region into a two-dimensional image may be performed when a difficult-to-observe region is detected. In such a case, one of left and right images may be used as an image common to the left and right images.

Figure 4E:
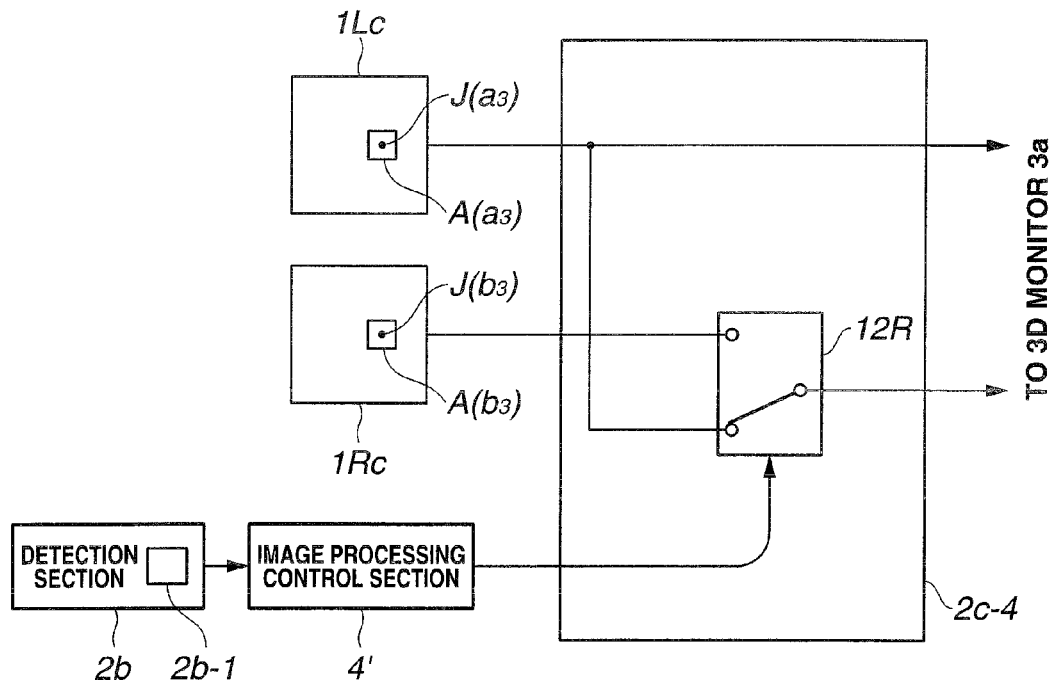
FIG. 4E is a diagram showing an example of a configuration in a case where the image treatment section performs processing on the entire image for conversion into a two-dimensional image.

FIG. 4E shows an example of a configuration in a case where the above-described image treatment processing 2c-4 is performed in the image treatment section 2c. Referring to FIG. 4E, the multipliers 13L and 13R and one switch 12L in the two switches are removed from the configuration shown in FIG. 4B. Image data from the frame memory 1Lc is inputted to the switch 12R. If a difficult-to-observe region exists, the same display as the left image is produced for the right image in the corresponding frame, thus making the difficult-to-observe region easier to observe.

Figure 10:
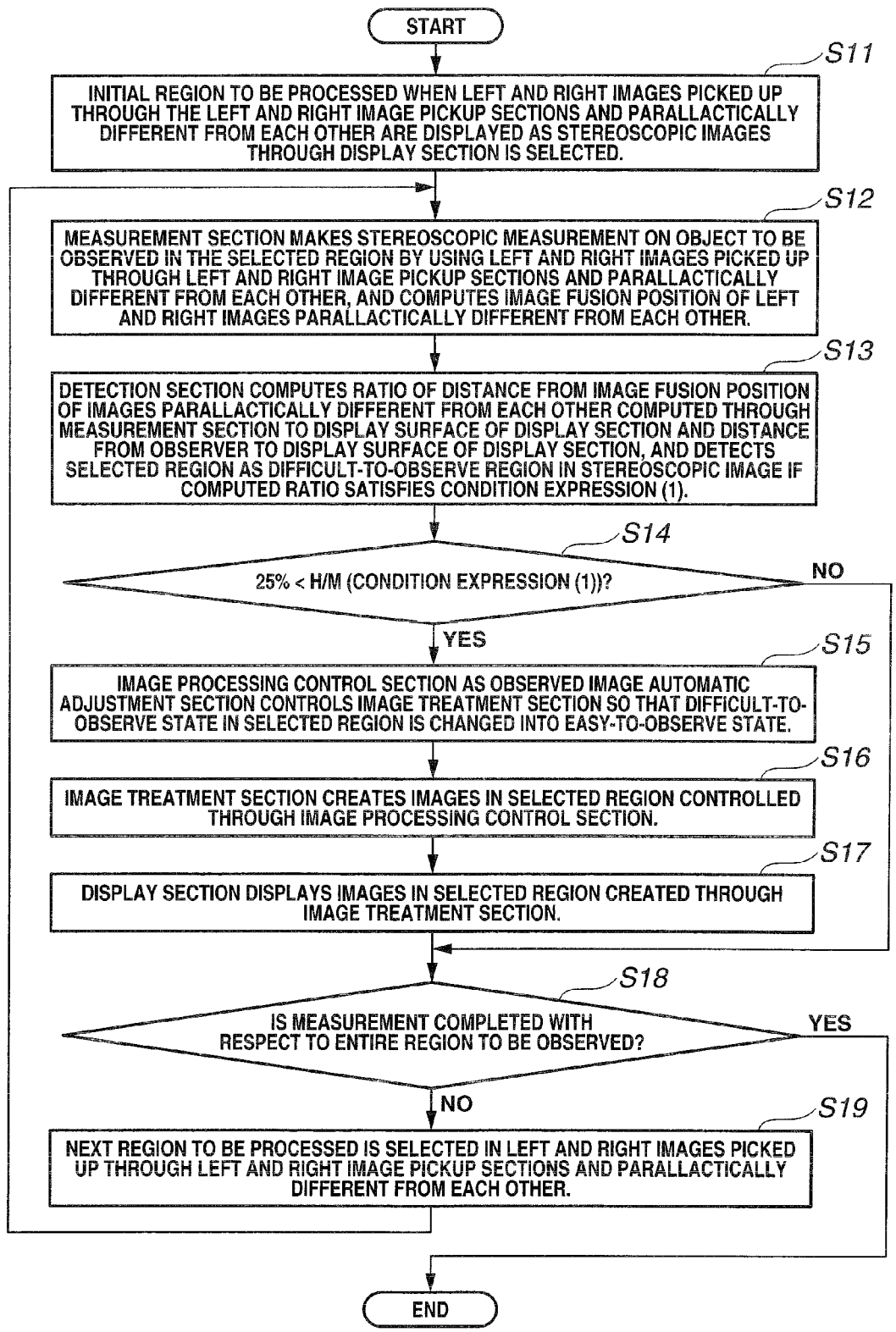
FIG. 10 is a flowchart showing a processing procedure for displaying images of an object to be observed shot with the stereoscopic image shooting and display system in the first embodiment.

In the stereoscopic image shooting and display system 11A in the first embodiment configured as described above, images obtained by performing processing by a processing procedure such as shown in FIG. 10 on images of the object 20 to be observed picked up through the image pickup sections 1 are displayed on the display section 3.

First, an initial region to be processed of left and right images picked up through the left-right pair of image pickup sections 1 and parallactically different from each other is selected when the left and right images are displayed as a stereoscopic image through the display section 3 (step S11).

Next, the measurement section 2a makes a stereoscopic measurement on the object 20 to be observed in the selected region by using the left and right images picked up through the left-right pair of image pickup sections 1 and parallactically different from each other, and computes the image fusion position of the left and right images parallactically different from each other (step S12).

Next, the detection section 2b computes the ratio H/M of the distance from the image fusion position of the images parallactically different from each other computed through the measurement section 2a to the display surface of the display section 3 and the distance from the observer 10 to the display surface of the display section 3, and detects the selected region as a difficult-to-observe region in the stereoscopic image if the computed ratio satisfies the condition expression (1) (25%<H/M) (steps S13, S14).

If the selected region is detected as a difficult-to-observe region in the stereoscopic image, the image processing control section 4' as the observed image automatic adjustment section controls the image treatment section 2c so that the difficult-to-observe state in the selected region is changed into an easy-to-observe state (step S15).

The image treatment section 2c creates images controlled so as to be easy-to-observe state (step S16).

Next, the display section 3 displays the images in the selected region controlled through the image processing control section 4' and created through the image treatment section 2c (step S17).

Next, a check is made as to whether or not selection has been completed with respect to the entire region (step S18). If selection has not been completed, the next region to be processed is selected in the left and right images picked up through the left-right pair of image pickup sections 1 and parallactically different from each other (step S19), and processing from step S12 to step S18 is repeated.

In this way, the observed image is made easy to see as a whole.

In the stereoscopic image shooting and display system 11A in the first embodiment, the image processing section 2 detects the existence/nonexistence of a difficult-to-observe region by using images picked up through the image pickup sections 1 and, if a difficult-to-observe region exists, the image processing control section 4' as control section controls the image processing section 2 so that the difficult-to-observe state in the selected region is changed into an easy-to-observe state, in a state where the distance between the optical axes of the left-right pair of optical systems parallactically different from each other is fixed.

Thus, the stereoscopic image shooting and display system 11A in the first embodiment is capable of dissolving a feeling of unnaturalness which an observer has in a stereoscopically observed image without thickening the image pickup sections 1 in the diametral direction.

Second Embodiment

The second embodiment of the present invention will be described with reference to FIGS. 11 to 14.

Figure 11:
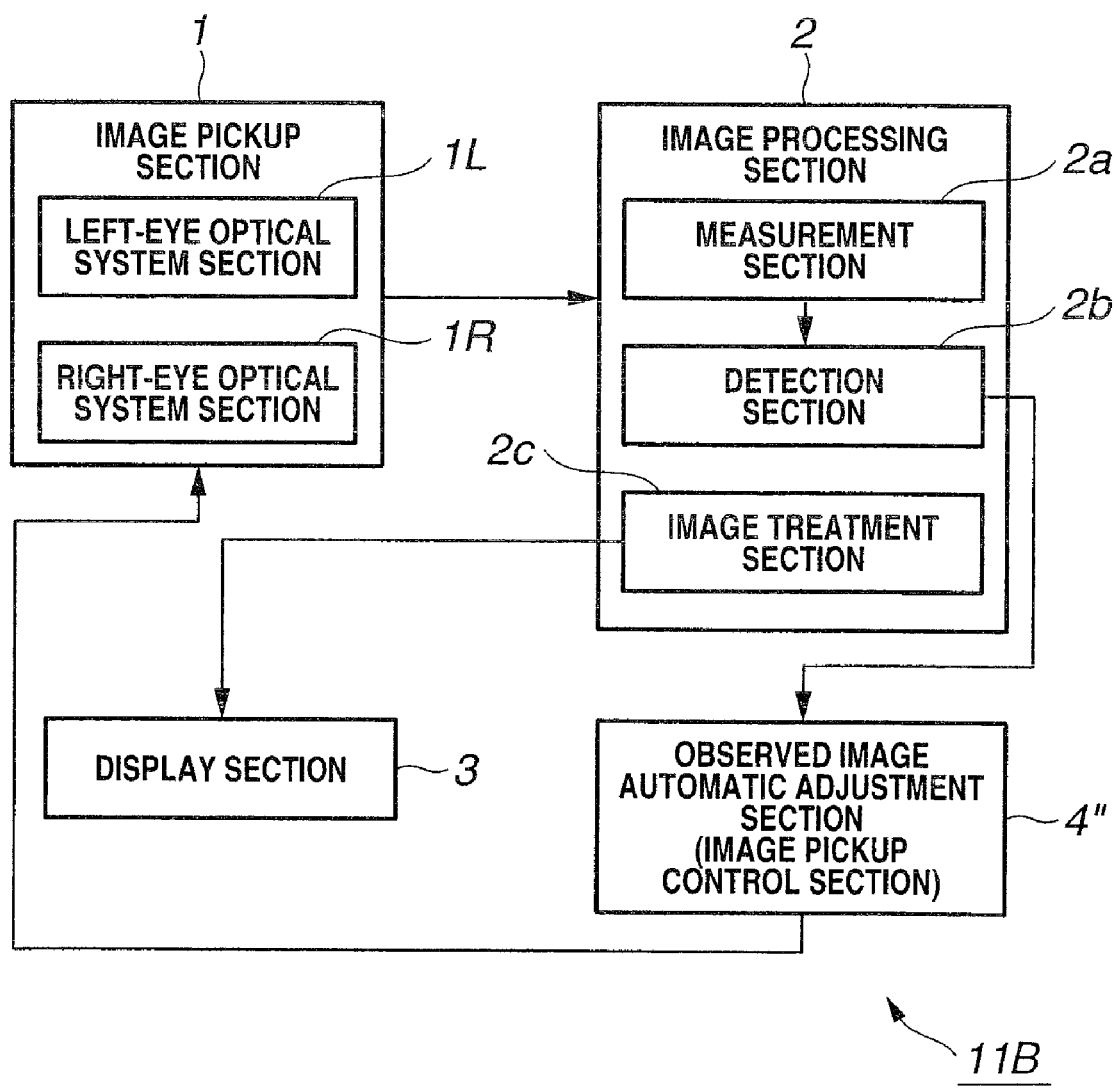
FIG. 11 is a block diagram schematically showing a configuration of a stereoscopic image shooting and display system according to a second embodiment of the present invention.

As shown in FIG. 11, a stereoscopic image shooting and display system 11B in the second embodiment has a left-right pair of image pickup sections 1, an image processing section 2 and a display section 3 and an observed image automatic adjustment section 4" as a control section.

The left-right pair of image pickup sections 1 are configured to be controlled in shooting through the observed image automatic adjustment section 4" described below.

Figure 12:
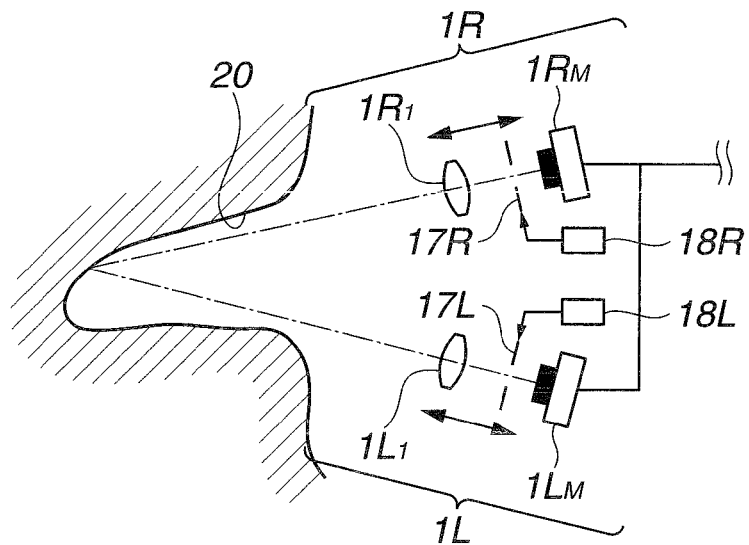
FIG. 12 is an explanatory diagram schematically showing an example of a configuration of an essential portion of the stereoscopic image shooting and display system shown in FIG. 11.

More specifically, for example, as shown in FIG. 12, the left-eye objective lens $1L_1$ and the right-eye objective lens $1R_1$ are disposed so as to be movable in the respective optical axis directions and capable of changing the positions of the focal points by being moved in the optical axis direction.

Figure 13:
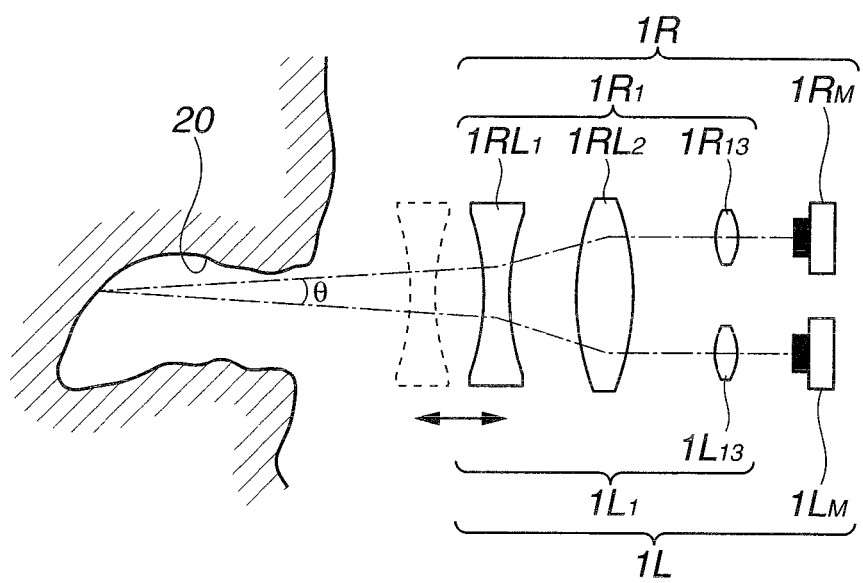
FIG. 13 is an explanatory diagram schematically showing another example of a configuration of an essential portion of the stereoscopic image shooting and display system shown in FIG. 11.

Also, the left-right pair of image pickup sections 1 may alternatively have, for example, common lenses $1RL_1$ and $1RL_2$, as shown in FIG. 13. The lens $1RL_1$ is disposed so as to be movable in the optical axis direction, and the focal length can be changed by moving the lens $1RL_1$ in the optical axis direction.

In FIG. 13, $1L_{13}$ and $1R_{13}$ represent lenses separately provided in the left-right pair of optical system sections 1L and 1R.

The image processing section 2 is configured of a measurement section 2a, a detection section 2b and an image treatment section 2c, similarly to the case in the first embodiment.

The display section 3 is configured to display images processed by the image processing section 2, similarly to the case in the first embodiment.

The observed image automatic adjustment section 4" functions as an image pickup control section to perform predetermined control on the left-right pair of image pickup sections 1 so that, when a difficult-to-observe region is detected through the detection section 2b, a predetermined image characteristic in the difficult-to-observe region in a stereoscopic image is changed to achieve an easy-to-observe state.

For example, as shown in FIG. 12, in a case where the objective lenses $1L_1$ and $1R_1$ in the optical system sections 1L and 1R provided in the left-right pair of image pickup sections 1 are movable, the positions of the focal points are controlled by moving the objective lenses $1L_1$ and $1R_1$ in the respective optical axis directions. The image of the difficult-to-observe region is thereby made unsharp.

A configuration may alternatively be adopted in which stop opening/closing mechanisms 18R and 18L are included for opening/closing stops 17R and 17L disposed at pupil positions in the optical system sections 1R and 1L provided in the left-right pair of image pickup sections 1. The stop opening/closing mechanisms 18R and 18L are controlled so as to open the stops 17R and 17L with respect to a difficult-to-observe region to reduce the depth of field and make the image of the difficult-to-observe region unsharp.

The stop opening/closing mechanisms 18R and 18L may also function as focus position control mechanism for controlling the positions of the focal points of the objective lenses $1L_1$ and $1R_1$ by moving the objective lenses $1L_1$ and $1R_1$ in the respective optical axis directions.

A case is conceivable in which an image in a "difficult-to-observe region" projects on the observer side to cause an observer to have a feeling of unnaturalness such as an oppressive sensation. Further, in some case, a projecting portion of an image blurs and becomes so excessively unsharp due to projection on the observer side that the image as a whole causes an observer to have a feeling of unnaturalness.

To reduce excessive unsharpness of an image in a "difficult-to-observe region", the locus position may be controlled, for example, by moving in the optical axis direction the lens $1RL_1$ common to the optical system sections 1R and 1L provided the left-right pair of image pickup sections in the example shown in FIG. 13 so that the image of the difficult-to-observe region excessively unsharp is made sharper.

On the other hand, to dissolve an oppressive sensation which an observer has due to projection of an image in a "difficult-to-observe region" to the observer side, the focus position may be controlled, for example, by moving in the optical axis direction the lens $1RL_1$ common to the optical system sections 1R and 1L provided the left-right pair of image pickup sections in the example shown in FIG. 13 so that the image of the difficult-to-observe region is made unsharp.

Also, difficulty in observation may be dissolved by moving in the optical axis direction the lens $1RL_1$ common to the optical system sections 1R and 1L so as to adjust the stereoscopic angle θ, as in the example shown in FIG. 13.

In other respects, the configuration of the stereoscopic image shooting and display system 11B in the second embodiment is generally the same as that of the stereoscopic image shooting and display system 11A in the first embodiment.

Figure 14:
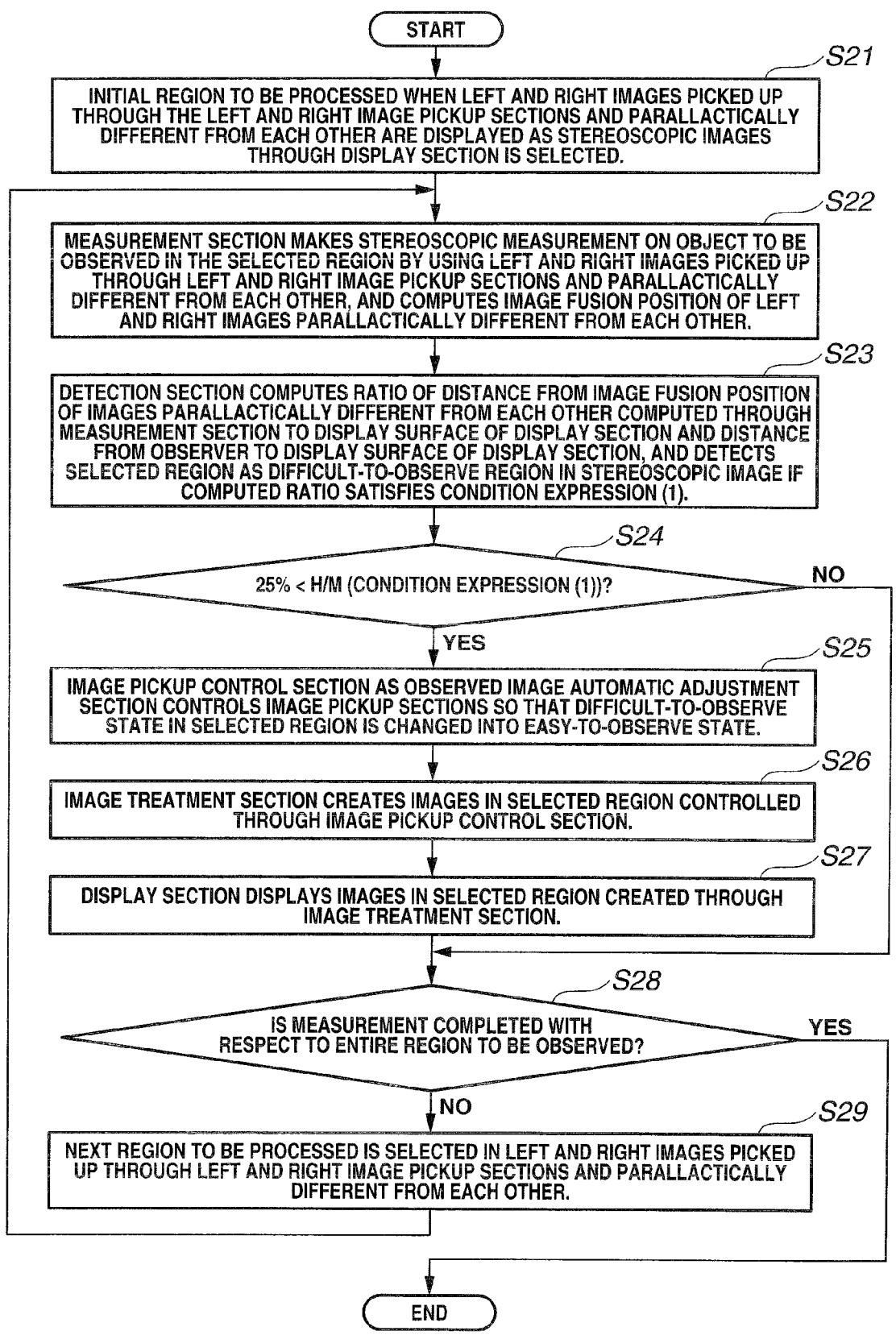
FIG. 14 is a flowchart showing a processing procedure for displaying images of an object to be observed shot with the stereoscopic image shooting and display system in the second embodiment.

In the stereoscopic image shooting and display system 11B in the second embodiment configured as described above, images obtained by performing processing by a processing procedure such as shown in FIG. 14 on images of the object 20 to be observed picked up through the image pickup sections 1 are displayed on the display section 3.

First, an initial region to be processed of left and right images picked up through the left-right pair of image pickup sections 1 and parallactically different from each other is selected when the left and right images are displayed as a stereoscopic image through the display section 3 (step S21).

Next, the measurement section 2a makes a stereoscopic measurement on the object 20 to be observed in the selected region by using the left and right images picked up through the left-right pair of image pickup sections 1 and parallactically different from each other, and computes the image fusion position of the left and right images parallactically different from each other (step S22).

Next, the detection section 2b computes the ratio H/M of the distance from the image fusion position of the images parallactically different from each other computed through the measurement section 2a to the display surface of the display section 3 and the distance from the observer 10 to the display surface of the display section 3, and detects the selected region as a difficult-to-observe region in the stereoscopic image if the computed ratio satisfies the condition expression (1) (25%<H/M) (steps S23, S24).

If the selected region is detected as a difficult-to-observe region in the stereoscopic image, the image processing control section 4" as the observed image automatic adjustment section controls the image pickup sections 1 so that the difficult-to-observe state in the selected region is changed into an easy to observe state (step S25).

Images controlled so as to be easy-to-observe state are picked up through the image pickup sections 1, and images obtained by performing predetermined processing on the picked up images are created through the image treatment section 2c (step S26).

Next, image pickup by the image pickup sections 1 is controlled through the image processing control section 4", and the display section 3 displays the images in the selected region controlled through the image treatment section 2c (step S27).

Next, a check is made as to whether or not selection has been completed with respect to the entire region (step S28). If selection has not been completed, the next region to be processed is selected in the left and right images picked up through the left-right pair of image pickup sections 1 and parallactically different from each other (step S29), and processing from step S22 to step S28 is repeated.

In this way, the observed image is made easy to see as a whole.

In the stereoscopic image shooting and display system 11B in the second embodiment, the image processing section 2 detects the existence/nonexistence of a difficult-to-observe region by using images picked up through the image pickup sections 1 and, if a difficult-to-observe region exists, the image processing control section 4" as the observed image automatic adjustment section controls the image pickup sections 1 so that the difficult-to-observe state in the selected region is changed into an easy-to-observe state, in a state where the distance between the optical axes of the left-right pair of optical systems parallactically different from each other is fixed. Thus, a feeling of unnaturalness which an observer has in a stereoscopically observed image can be dissolved without thickening the image pickup sections 1 in the diametral direction.

Third Embodiment

Figure 15:
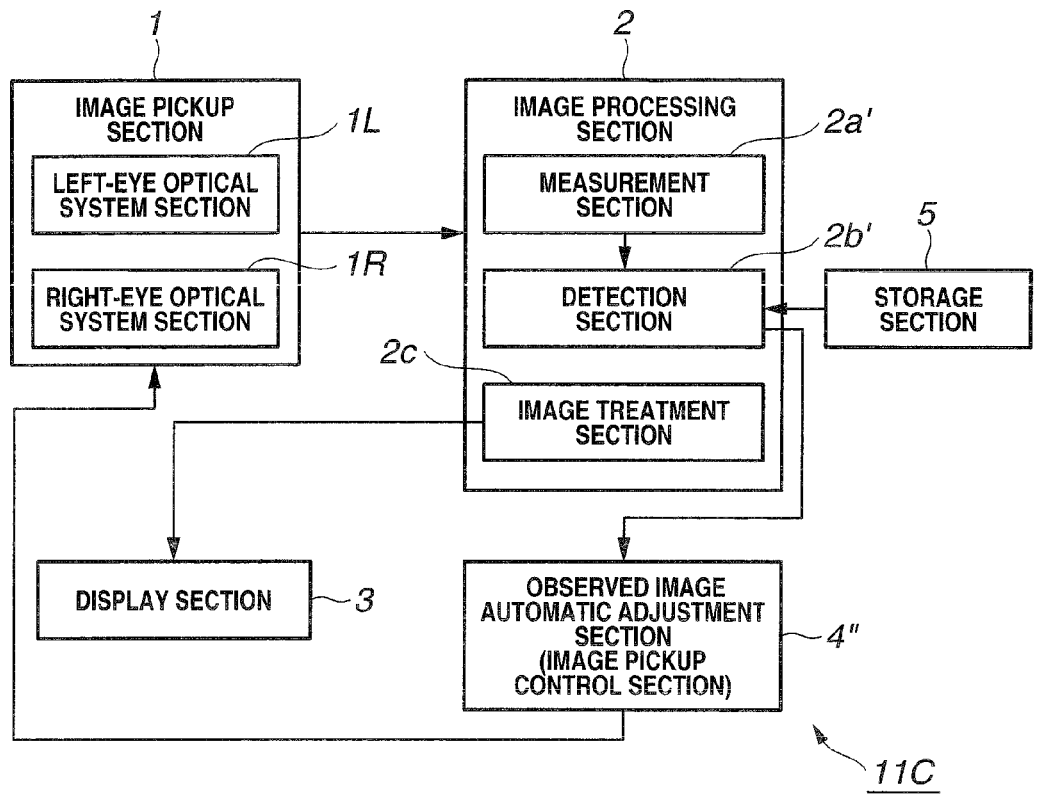
FIG. 15 is a block diagram schematically showing a configuration of a stereoscopic image shooting and display system according to a third embodiment of the present invention.
Figure 16:
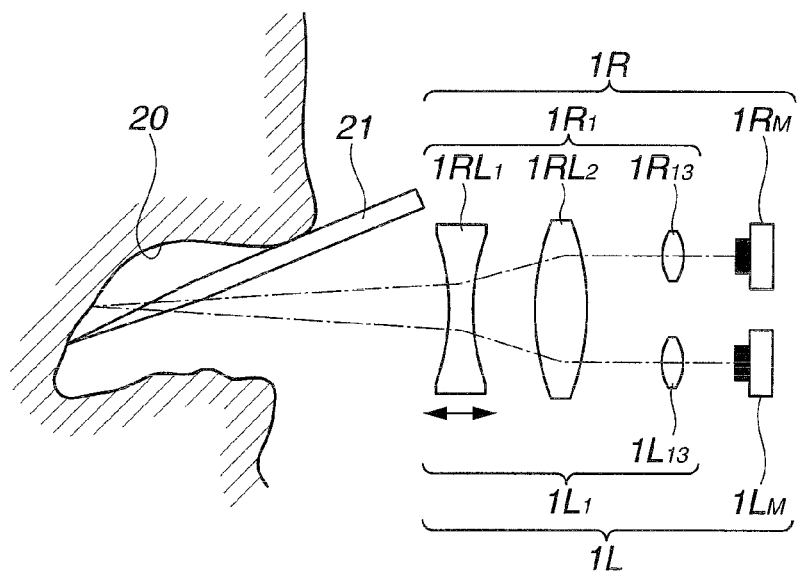
FIG. 16 is an explanatory diagram schematically showing an example of a configuration of an essential portion in the stereoscopic image shooting and display system shown in FIG. 15.

FIG. 15 is a block diagram schematically showing a configuration of a stereoscopic image shooting and display system 11C according to the third embodiment of the present invention. FIG. 16 is an explanatory diagram schematically showing an example of a configuration of an essential portion in the stereoscopic image shooting and display system 11C shown in FIG. 15. FIG. 17 is a flowchart showing a processing procedure for displaying images of an object to be observed shot with the stereoscopic image shooting and display system 11C in the third embodiment.

As shown in FIG. 15, the stereoscopic image shooting and display system 11C in the third embodiment has a left-right pair of image pickup sections 1, an image processing section 2 and a display section 3, an observed image automatic adjustment section 4", and a storage section 5.

The left-right pair of image pickup sections 1 are configured so as to be controlled in shooting through the observed image automatic adjustment section 4" described below.

More specifically, for example, as shown in FIG. 16, the left-right pair of image pickup sections 1 have common lenses $1RL_1$ and $1RL_2$; the lens $1RL_1$ is disposed so as to be movable in the optical axis direction; and image pickup sections 1 are configured so as to be capable of changing the focal length by moving the lens $1RL_1$ in the optical axis direction.

In the storage section 5, at least one physical quantity (e.g., the shape, size, color, three-dimensional shape or spectral characteristic) of an object which, when left and right images parallactically different from each other are displayed as a stereoscopic image through the display section 3, produces a difficult-to-observe region in the stereoscopic image (an operating knife 21, which is a treatment instrument, in the case shown in FIG. 16) are recorded in advance.

The image processing section 2 is configured of a measurement section 2a', a detection section 2b' and an image treatment section 2c.

The measurement section 2a' has a function to measure at least one physical quantity (e.g., the shape, size, color, three-dimensional shape or spectral characteristic) of the object 20 to be observed (including the operating knife 21, which is a treatment instrument inserted in a body portion on which an operation is performed).

When left and right images parallactically different from each other are displayed through the display section 3 by being fused into the stereoscopic image, the detection section 2b' compares the physical quantity of the object 20 to be observed (including the operating knife 21 in this embodiment) measured through measurement section 2a' with the physical quantity of the object (the operating knife 21 in this embodiment) stored in advance in the storage section 5 with respect to each region in the stereoscopic image.

The detection section 2b' detects the region in the stereoscopic image as a difficult-to-observe region in the stereoscopic image if the measured physical quantity of the object 20 to be observed and the physical quantity of the object (the operating knife 21) stored in the storage section 5 in advance coincide with each other.

The display section 3 is configured to display images processed by the image processing section 2, similarly to the case in the first embodiment.

A treatment instrument such as the operating knife 21 is elongated in shape and strongly reflects light. Therefore such an object is often difficult to stereoscopically observe.

For this reason, in the stereoscopic image shooting and display system 11C in the third embodiment, physical quantities such as the shape, size, color, three-dimensional shape and spectral characteristic of a treatment instrument are stored in the storage section 5 in advance. Also, in the stereoscopic image shooting and display system 11C, the measurement section 2a' measures these physical quantities in the region in the object 20 to be observed during observation of the object 20 to be observed.

The physical quantities of the object 20 to be observed measured through the measurement section 2a' and the physical quantities of the object 21 stored in the storage section 5 are compared with each other by the detection section 2b'. If these physical quantities coincide with each other, the region in the object is detected as a difficult-to-observe region.

Predetermined control is performed on the left-right pair of image pickup sections 1 through the observed image automatic adjustment section 4" so that the region is made easier to observe, as in the stereoscopic image shooting and display system 11B in the second embodiment. Image pickup by the image pickup sections 1 is thus controlled and images created through the image treatment section 2c are displayed on the display section 3.

In other respects, the configuration of the stereoscopic image shooting and display system 11C in the third embodiment is generally the same as that of the stereoscopic image shooting and display system 11B in the second embodiment.

In the stereoscopic image shooting and display system 11C in the third embodiment configured as described above, images obtained by performing processing by a processing procedure such as shown in FIG. 17 on images of the object 20 to be observed picked up through the image pickup sections 1 are displayed on the display section 3.

First, an initial region to be processed of left and right images picked up through the left-right pair of image pickup sections 1 and parallactically different from each other is selected when the left and right images are displayed as a stereoscopic image through the display section 3 (step S31).

Next, the measurement section 2a' makes a stereoscopic measurement on the object 20 to be observed in the selected region by using the left and right images picked up through the left-right pair of image pickup sections 1 and parallactically different from each other, and measures at least one physical quantity of the object 20 to be observed (step S32).

Next, the detection section 2b' compares the physical quantity measured through the measurement section 2a' with the physical quantity of an object stored in the storage section 5 in advance. If the measured physical quantity coincides with the stored physical quantity, the detection section 2b' detects the selected region as a difficult-to-observe region in the stereoscopic image (steps S33, S34).

If the selected region is detected as a difficult-to-observe region in the stereoscopic image, the image processing control section 4" as the observed image automatic adjustment section controls the image pickup sections 1 so that the difficult-to-observe state in the selected region is changed into an easy-to-observe state (step S35).

Images controlled so as to be easy-to-observe state are picked up through the image pickup sections 1, and images obtained by performing predetermined processing on the picked up images are created through the image treatment section 2c (step S36).

Next, image pickup by the image pickup sections 1 is controlled through the image processing control section 4", and the display section 3 displays the images in the selected region controlled through the image treatment section 2c (step S37).

Next, a check is made as to whether or not selection has been completed with respect to the entire region (step S38). If selection has not been completed, the next region to be processed is selected in the left and right images picked up through the left-right pair of image pickup sections 1 and parallactically different from each other (step S39), and processing from step S32 to step S38 is repeated.

In this way, the observed image is made easy to see as a whole.

In the stereoscopic image shooting and display system 11C in the third embodiment, the image processing section 2 detects the existence/nonexistence of a difficult-to-observe region by using images picked up through the image pickup sections 1 and, if a difficult-to-observe region exists, the image processing control section 4" as the observed image automatic adjustment section controls the image pickup sections 1 so that the difficult-to-observe state in the selected region is changed into an easy-to-observe state, in a state where the distance between the optical axes of the left-right pair of optical systems parallactically different from each other is fixed.

Thus, a feeling of unnaturalness which an observer has in a stereoscopically observed image can be dissolved without thickening the image pickup sections 1 in the diametral direction.

Also, in the stereoscopic image shooting and display system 11C in the third embodiment, the physical quantities of the object 20 to be observed measured through the measurement section 2a' are compared with the physical quantities of an object stored in the storage section 5 in advance and, the selected region is detected as a difficult-to-observe region in the stereoscopic image if these physical quantities coincide with each other. For example, in a case where a body portion on which an operation is performed by using a treatment instrument is observed during the operation, difficulty in observation under the presence of the treatment instrument can be dissolved in the above-described way.

The stereoscopic image shooting and display system of the present invention is not limited to the configurations of the above-described embodiments. Needless to say, a certain combination of characteristic configurations in the stereoscopic image shooting and display systems in the embodiments may be made.

For example, the observed image automatic adjustment section 4 may be configured to function both as the image processing control section 4' shown in the first embodiment and as the image pickup control section 4" shown in the second and third embodiments, and selection between the functions of the observed image automatic adjustment section is made according to observation use through a selection section such as a switch.

Further, the image processing section 2 may be configured of the measurement section 2a and the detection section 2b shown in the first and second embodiments and the measurement section 2a', the detection section 2b' and the storage section 5 shown in the third embodiment, and selection between the functions of the observed image automatic adjustment section is made according to observation use through a selection section such as a switch.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A stereoscopic image shooting and display system enabling observation of a stereoscopic image of an object to be observed, comprising:

a left-right pair of image pickup sections having a left-right pair of optical systems with a parallax;

an image processing section which performs predetermined image processing on left and right images picked up through the left-right pair of image pickup sections and parallactically different from each other, and outputs the processed images to a display section which displays images;

the image processing section having a measurement section having at least a function to make a stereoscopic measurement on the object to be observed, a detection section which, when the left and right images parallactically different from each other are displayed as a stereoscopic image through the display section, detects the existence/nonexistence of a difficult-to-observe region in the stereoscopic image on the basis of results obtained through the measurement section, and an image treatment section which performs a predetermined image treatment on the left and right images picked up through the image pickup sections and parallactically different from each other; and a control section which, when the difficult-to-observe region is detected through the detection section, controls the image pickup sections or the image processing section so that image display on the display section is performed by changing the detected difficult-to-observe state in the difficult-to-observe region into an easy-to-observe state, in a state where the distance between the optical axes of the left-right pair of optical systems with a parallax is fixed.

2. The stereoscopic image shooting and display system according to claim 1, wherein the measurement section has a function to compute an image fusion position of the left and right images parallactically different from each other, and wherein the detection section computes, with respect to each region in the stereoscopic image when the left and right images are displayed as the stereoscopic image through the display section, the ratio of the second distance from a display surface of the display section to the image fusion position at which the left and right images parallactically different from each other computed through the measurement section are fused into one and the first distance from an observer to the display surface of the display section, and detects the region as a difficult-to-observe region in the stereoscopic image if the computed ratio satisfies the following condition expression (1):

$$25\% < H/M \qquad (1)$$

where M is the first distance from the observer to the display surface of the display section, and H is the second distance from the display surface of the display section to the image fusion position of the left and right images parallactically different from each other computed through the measurement section.

3. The stereoscopic image shooting and display system according to claim 1, wherein the measurement section has a function to compute an image fusion position of the left and right images parallactically different from each other, and wherein the detection section computes, with respect to each region in the stereoscopic image when the left and right images parallactically different from each other are displayed as the stereoscopic image through the display section, the ratio of the second distance from a display surface of the display section to the image fusion position at which the left and right images parallactically different from each other computed through the measurement section are fused into one and the first distance from an observer to the display surface of the display section, and detects the region as a difficult-to-observe region in the stereoscopic image if the computed ratio satisfies the following condition expression (2):

$$15\% < H/M \qquad (2)$$

where M is the first distance from the observer to the display surface of the display section, and H is the second distance from the display surface of the display section to the image fusion position of the left and right images parallactically different from each other computed through the measurement section.

4. The stereoscopic image shooting and display system according to claim 1, wherein the control section includes an image processing control section which makes the image treatment section convert a predetermined image characteristic in the difficult-to-observe region in the stereoscopic image so as to achieve an easy-to-observe state.

5. The stereoscopic image shooting and display system according to claim 2, wherein the control section includes an image processing control section which makes the image treatment section convert a predetermined image characteristic in the difficult-to-observe region in the stereoscopic image so as to achieve an easy-to-observe state.

6. The stereoscopic image shooting and display system according to claim 4, wherein the image processing control section makes the image treatment section convert the difficult-to-observe region in the stereoscopic image from a three-dimensional image into a two-dimensional image.

7. The stereoscopic image shooting and display system according to claim 5, wherein the image processing control section makes the image treatment section convert the difficult-to-observe region in the stereoscopic image from a three-dimensional image into a two-dimensional image.

8. The stereoscopic image shooting and display system according to claim 4, wherein the image processing control section makes the image treatment section convert the entire region in the stereoscopic image from a three-dimensional image into a two-dimensional image.

9. The stereoscopic image shooting and display system according to claim 4, wherein the image processing control section makes the image treatment section change the brightness in the difficult-to-observe region in the stereoscopic image.

10. The stereoscopic image shooting and display system according to claim 5, wherein the image processing control section makes the image treatment section change the brightness in the difficult-to-observe region in the stereoscopic image.

11. The stereoscopic image shooting and display system according to claim 4, wherein the image processing control section makes the image treatment section change a frequency characteristic in the difficult-to-observe region in the stereoscopic image.

12. The stereoscopic image shooting and display system according to claim 5, wherein the image processing control section makes the image treatment section change a frequency characteristic in the difficult-to-observe region in the stereoscopic image.

13. The stereoscopic image shooting and display system according to claim 1, wherein the control section comprises an image pickup control section which performs predetermined control on the left-right pair of image pickup sections so that a predetermined image characteristic in the difficult-to-observe region in the stereoscopic image becomes easy-to-observe.

14. The stereoscopic image shooting and display system according to claim 2, wherein the control section comprises an image pickup control section which performs predetermined control on the left-right pair of image pickup sections so that a predetermined image characteristic in the difficult-to-observe region in the stereoscopic image becomes easy-to-observe.

15. The stereoscopic image shooting and display system according to claim 13, wherein the image pickup control section controls stops of optical systems provided in the left-right pair of image pickup sections.

16. The stereoscopic image shooting and display system according to claim 13, wherein the image pickup control section controls focus positions of the optical systems provided in the left-right pair of image pickup sections.

17. The stereoscopic image shooting and display system according to claim 13, wherein the image pickup sections have an optical member common to the left-right pair of optical systems, and the image pickup control section controls a focus position through the common optical member provided in the left-right pair of image pickup sections.

18. The stereoscopic image shooting and display system according to claim 13, further comprising a storage section which stores in advance at least one physical quantity of an object which can be a cause of generation of a difficult-to-observe region in the stereoscopic image when the left and right images parallactically different from each other are displayed as the stereoscopic image through the display section,
  wherein the measurement section has a function to measure at least one physical quantity of the object to be observed, and
  wherein the detection section compares, with respect to each region in the stereoscopic image when the left and right images parallactically different from each other are displayed as the stereoscopic image through the display section, the physical quantity of the object to be observed measured through the measurement section with the physical quantity of the object stored in the storage section in advance, and detects the region as a difficult-to-observe region in the stereoscopic image if the physical quantities coincide with each other.

19. The stereoscopic image shooting and display system according to claim 18, wherein the physical quantity is one of a shape size, a color, a three-dimensional shape and a spectral characteristic.

20. The stereoscopic image shooting and display system according to claim 18, wherein objects whose physical quantities are to be stored by the storage section include a treatment instrument.

* * * * *